US010413693B2

(12) United States Patent
Prentice et al.

(10) Patent No.: US 10,413,693 B2
(45) Date of Patent: Sep. 17, 2019

(54) NASAL MASK INTERFACE ASSEMBLY

(71) Applicant: Fisher & Paykel Healthcare Limited, Auckland (NZ)

(72) Inventors: Craig Robert Prentice, Auckland (NZ); Bernard Tsz Lun Ip, Auckland (NZ); Richard John Boyes, Auckland (NZ); Thomas Mark Richardson, Auckland (NZ); Gareth Thomas McDermott, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 41 days.

(21) Appl. No.: 15/610,484

(22) Filed: May 31, 2017

(65) Prior Publication Data

US 2017/0266403 A1 Sep. 21, 2017

Related U.S. Application Data

(63) Continuation of application No. 14/127,940, filed as application No. PCT/NZ2012/000114 on Jun. 29, 2012.

(Continued)

(51) Int. Cl.
*A61M 16/06* (2006.01)
*A61M 16/08* (2006.01)
*A61M 16/00* (2006.01)

(52) U.S. Cl.
CPC .... *A61M 16/0616* (2014.02); *A61M 16/0057* (2013.01); *A61M 16/06* (2013.01);
(Continued)

(58) Field of Classification Search
CPC ...... A61M 2016/0661; A61M 16/0622; A61M 16/0616; A61M 16/0825; A61M 16/06;
(Continued)

(56) References Cited

U.S. PATENT DOCUMENTS 2,228,218 A 1/1941 Schwartz
2,415,846 A 2/1947 Randall
(Continued)

FOREIGN PATENT DOCUMENTS

AU 2006284507 B2 3/2007
CN 1784250 A 6/2006
(Continued)

OTHER PUBLICATIONS

International Search Report; Application No. PCT/NZ2012000114; dated Jun. 29, 2012.
(Continued)

*Primary Examiner* — Tan-Uyen T Ho
*Assistant Examiner* — Victoria Murphy
(74) *Attorney, Agent, or Firm* — Knobbe Martens Olson & Bear LLP

(57) ABSTRACT

An interface assembly comprises a nasal mask that includes a seal having a rolling portion. The rolling portion of the seal rolls over a portion of a clip that secures the seal to a frame. The frame has a ball and socket connection to a connector. The connector comprises an elbow having integrally formed exhaust holes and a swivel.

20 Claims, 22 Drawing Sheets

Related U.S. Application Data

(60) Provisional application No. 61/504,061, filed on Jul. 1, 2011.

(52) U.S. Cl.
CPC .... *A61M 16/0633* (2014.02); *A61M 16/0683* (2013.01); *A61M 16/0816* (2013.01); *A61M 16/0825* (2014.02); *A61M 2205/42* (2013.01)

(58) Field of Classification Search
CPC .......... A61M 16/0633; A61M 16/0816; A61M 16/0683; A61M 16/0057; A61M 2205/42
See application file for complete search history.

(56) References Cited

U.S. PATENT DOCUMENTS

| | | | |
|---|---|---|---|
| 3,037,501 A | 6/1962 | Miller | |
| 4,167,185 A | 9/1979 | Lewis | |
| 4,384,577 A * | 5/1983 | Huber | A41D 13/1146 128/206.19 |
| 5,349,949 A | 9/1994 | Schegerin | |
| 5,353,789 A | 10/1994 | Schlobohm | |
| D377,089 S | 12/1996 | Starr | |
| 5,921,239 A | 7/1999 | McCall et al. | |
| 6,123,071 A | 9/2000 | Berthon-Jones | |
| 6,374,826 B1 | 4/2002 | Gunaratnam et al. | |
| 6,467,483 B1 | 10/2002 | Kopacko et al. | |
| D476,732 S | 7/2003 | Smart | |
| 6,651,663 B2 | 11/2003 | Barnett et al. | |
| D486,226 S | 2/2004 | Guney et al. | |
| D498,529 S | 11/2004 | Kwok | |
| 6,851,428 B2 | 2/2005 | Dennis | |
| 7,237,551 B2 | 7/2007 | Ho et al. | |
| D549,322 S | 8/2007 | Stallard et al. | |
| D555,785 S | 11/2007 | McAuley et al. | |
| D557,411 S | 12/2007 | Smart et al. | |
| D558,334 S | 12/2007 | Stallard et al. | |
| D582,546 S | 12/2008 | Fujiura et al. | |
| D583,930 S | 12/2008 | McAuley et al. | |
| D586,458 S | 2/2009 | Kooij et al. | |
| D586,906 S | 2/2009 | Stallard et al. | |
| 7,523,754 B2 | 4/2009 | Lithgow et al. | |
| D595,841 S | 7/2009 | McAuley et al. | |
| D597,661 S | 8/2009 | Reid et al. | |
| 7,665,464 B2 | 2/2010 | Kopacko et al. | |
| D612,483 S | 3/2010 | Chang | |
| D612,932 S | 3/2010 | Davidson et al. | |
| D614,763 S | 4/2010 | Maurer et al. | |
| D624,642 S | 9/2010 | Collazo et al. | |
| 7,827,990 B1 | 11/2010 | Melidis et al. | |
| 7,861,718 B2 | 1/2011 | Janbakhsh et al. | |
| D639,419 S | 6/2011 | Eves et al. | |
| D639,932 S | 6/2011 | D'Souza et al. | |
| 7,971,590 B2 | 7/2011 | Frater et al. | |
| D645,955 S | 9/2011 | Kooij et al. | |
| D653,328 S | 1/2012 | Eves et al. | |
| 8,220,459 B2 | 7/2012 | Davidson et al. | |
| 8,230,861 B2 | 7/2012 | Ho | |
| D665,494 S | 8/2012 | Stallard et al. | |
| 8,245,711 B2 | 8/2012 | Matula, Jr. et al. | |
| 8,297,283 B2 | 10/2012 | Hitchcock et al. | |
| D693,459 S | 11/2013 | Prentice | |
| D706,413 S | 6/2014 | Veliss | |
| D716,505 S | 10/2014 | Wu | |
| D716,506 S | 10/2014 | Wu | |
| 8,869,797 B2 | 10/2014 | Davidson et al. | |
| 8,931,484 B2 | 1/2015 | Melidis et al. | |
| D730,511 S | 5/2015 | Mark | |
| D740,935 S | 10/2015 | Cullen | |
| D754,328 S | 4/2016 | Bowsher | |
| D770,035 S | 10/2016 | Prentice | |
| D794,772 S | 8/2017 | Cullen | |
| 2004/0112386 A1 | 6/2004 | Griffiths | |
| 2006/0118117 A1 * | 6/2006 | Berthon-Jones | A61M 16/06 128/206.21 |
| 2006/0207599 A1 * | 9/2006 | Busch | A61M 16/06 128/206.24 |
| 2007/0044804 A1 | 3/2007 | Matula, Jr. et al. | |
| 2007/0163594 A1 | 7/2007 | Ho et al. | |
| 2007/0215161 A1 | 9/2007 | Frater et al. | |
| 2007/0267017 A1 | 11/2007 | McAuley et al. | |
| 2008/0110464 A1 | 5/2008 | Davidson et al. | |
| 2008/0257354 A1 | 10/2008 | Davidson et al. | |
| 2009/0139526 A1 | 6/2009 | Melidis et al. | |
| 2009/0183734 A1 | 7/2009 | Kwok | |
| 2010/0122701 A1 | 5/2010 | Gunaratnam et al. | |
| 2014/0096774 A1 | 4/2014 | Olsen | |
| 2014/0174446 A1 | 6/2014 | Prentice et al. | |

FOREIGN PATENT DOCUMENTS

| | | |
|---|---|---|
| CN | 101155610 A | 4/2008 |
| CN | 101227947 A | 7/2008 |
| CN | 101242866 A | 8/2008 |
| CN | 101301505 A | 11/2008 |
| CN | 101370557 A | 2/2009 |
| CN | 101954140 A | 1/2011 |
| EP | 1 258 266 A1 | 11/2002 |
| EP | 1 982 740 A2 | 10/2008 |
| GB | 2 393 126 B | 11/2004 |
| JP | 2008-526391 A | 7/2008 |
| NZ | 551715 | 2/2011 |
| WO | WO 2001/32250 A1 | 5/2001 |
| WO | WO 2004/071565 A1 | 8/2004 |
| WO | WO 2005/094928 A1 | 10/2005 |
| WO | WO 2005/123166 A1 | 12/2005 |
| WO | WO 2006/074513 A1 | 7/2006 |
| WO | WO 2007/145534 A1 | 12/2007 |
| WO | WO 2010/009877 A1 | 1/2010 |
| WO | WO 2010/071453 A1 | 6/2010 |
| WO | WO 2010/135785 A1 | 12/2010 |

OTHER PUBLICATIONS

International Preliminary Report on Patentability; Application No. PCT/NZ2012/000114; filed Jun. 29, 2012.
Communication of the Preliminary Search Report; French Filing No. 1256321, dated Jan. 28, 2014, 11 pages.
European Exam Report; German Application No. 12807770.8, dated Dec. 12, 2016, 6 pages.
European Exam Report; German Application No. 12807770.8, dated Feb. 3, 2016, 4 pages.
Examination report No. 3 for your standard patent application; Australian Application No. 2012278416, dated Feb. 17, 2017, 5 pages.
International Search Report, Int'l Application No. PCT/IB2012/000858, dated Aug. 13, 2012, 9 pages.
Notification of the First Office Action; Chinese Application No. 201280040172.0, dated Jul. 15, 2015, 9 pages.
Notification of the Third Office Action; Chinese Application No. 201280040172.0, dated Nov. 30, 2016, 2 pages.
Office Action; French Application No. 1553942, dated Jun. 18, 2015, 2 pages.
Office Action; Chinese Application No. 201280040172.0, dated May 20, 2016, 8 pages.
Official Letter; French Filing No. 1256321, dated Sep. 10, 2012, 2 pages.
Official Letter; French Filing No. 1256321, dated Oct. 16, 2012, 4 pages.
Official Letter; French Filing No. 1256321, dated Sep. 10, 2012, 1 page.
Partial European Search Report; German Application No. 12807770.8, dated Jul. 1, 2015, 7 pages.
Patent Examination Report No. 1; Australian Application No. 2012278416, dated Feb. 22, 2016, 4 pages.
Patent Examination Report No. 2; Australian Application No. 2012278416, dated Sep. 14, 2016, 4 pages.
Search Report; Chinese Application No. 201280040172.0, dated Nov. 30, 2016, 10 pages.

(56) References Cited

OTHER PUBLICATIONS

Text Portion of the Notification of the Third Office Action; Chinese Application No. 201280040172.0, dated Nov. 30, 2016, 2 pages.
The Preliminary Search Report; French Filing No. 1256321, dated Apr. 4, 2014, 1 page.
Translation of Decision of Rejection; Japanese Application No. 2014-518473, dated Jan. 17, 2017, 4 pages.
Translation of Office Action Notice of Reason for Rejection; Japanese Application No. 2014-518473, dated May 6, 2016, 11 pages.
Petition for Inter Partes Review of U.S. Pat. No. 9,242,062, *Fisher & Paykel Healthcare Limited* v. *Resmed Limited,* Case No. IPR2017-00272, as filed Nov. 15, 2016, 92 pages.
Patent Owner Resmed Limited's Preliminary Response, *Fisher & Paykel Healthcare Limited* v. *Resmed Limited,* Case No. IPR2017-00272, as filed Feb. 28, 2017, 42 pages.
Decision Instituting Inter Partes Review, *Fisher & Paykel Healthcare Limited* v. *Resmed Limited,* Case No. IPR2017-00272, as entered May 4, 2017, 29 pages.
Patent Owner Resmed Limited's Response, *Fisher & Paykel Healthcare Limited* v. *Resmed Limited,* Case No. IPR2017-00272, as filed Aug. 4, 2017, 75 pages.
Fisher & Paykel Healthcare's Reply to Resmed's Patent Owner Response, *Fisher & Paykel Healthcare Limited* v. *Resmed Limited,* Case No. IPR2017-00272, as filed Nov. 6, 2017, 39 pages.

\* cited by examiner

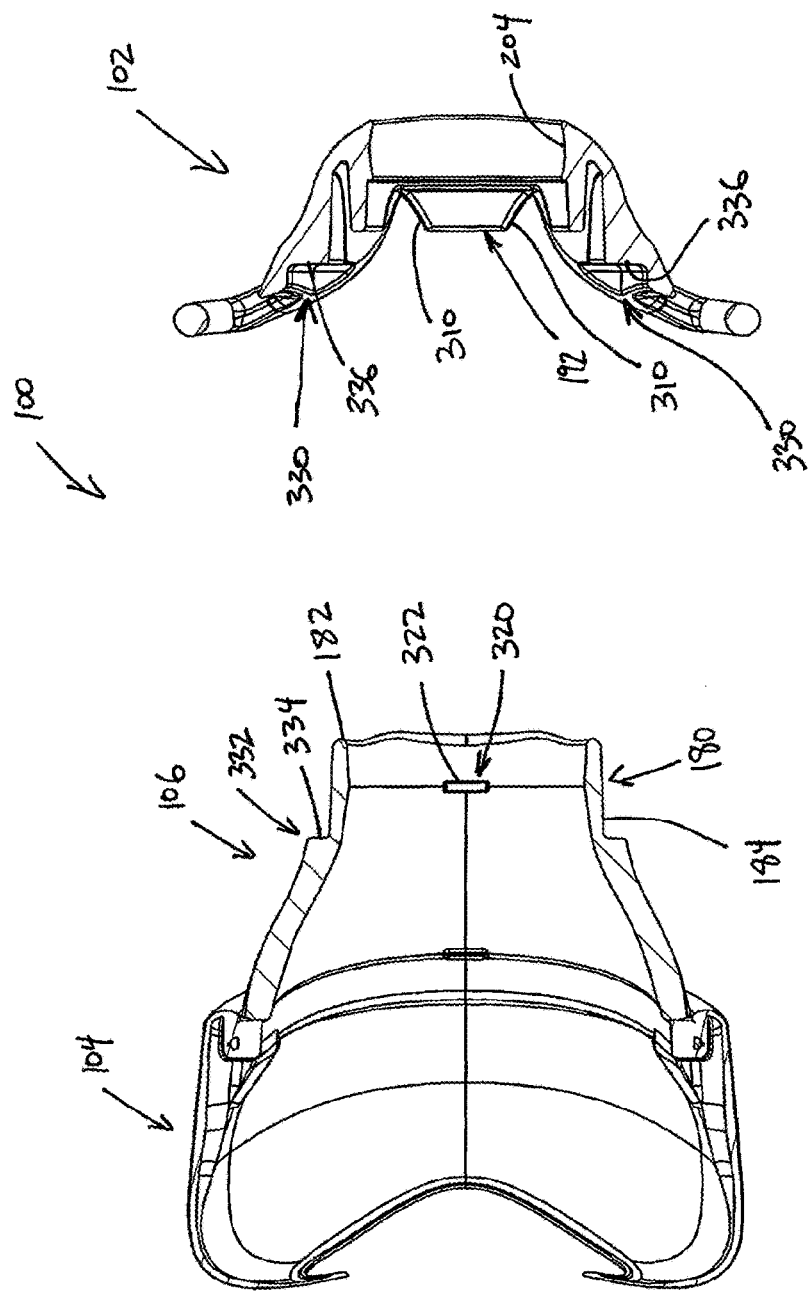

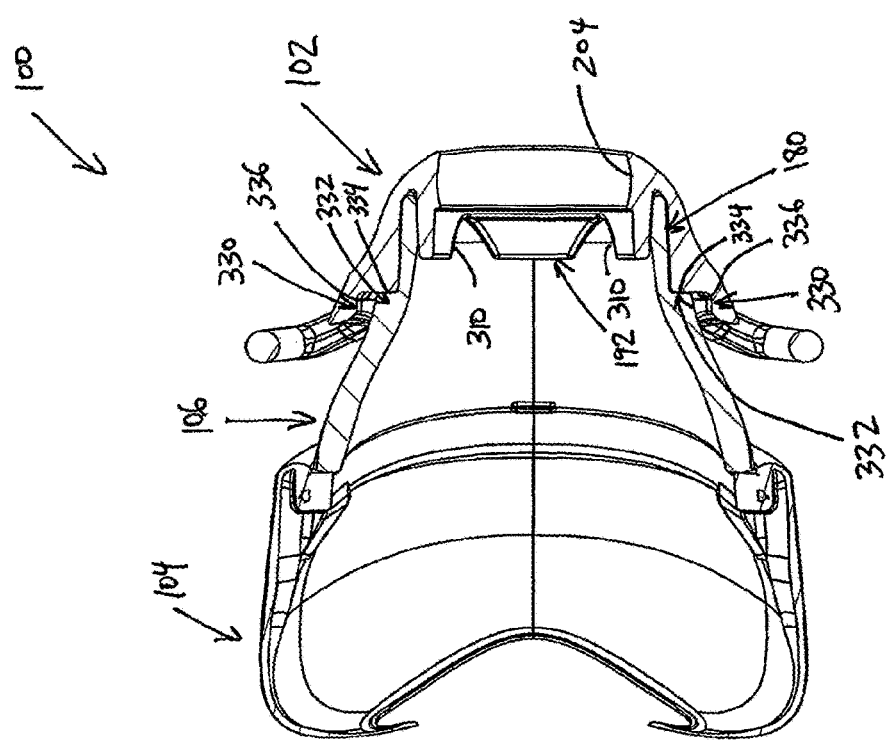

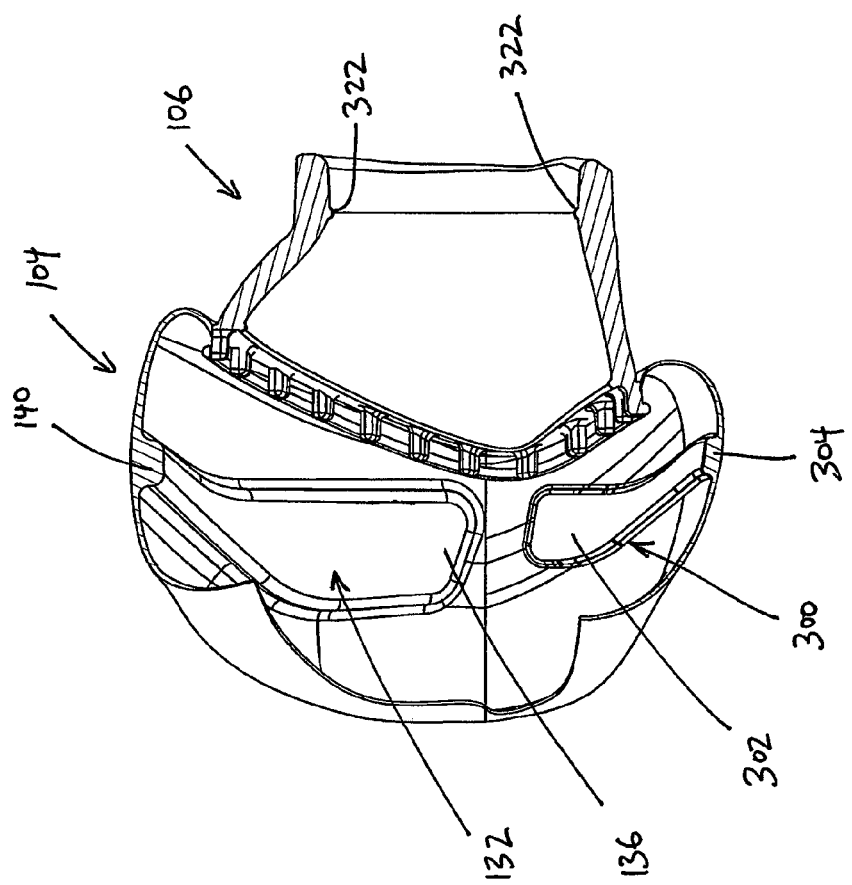

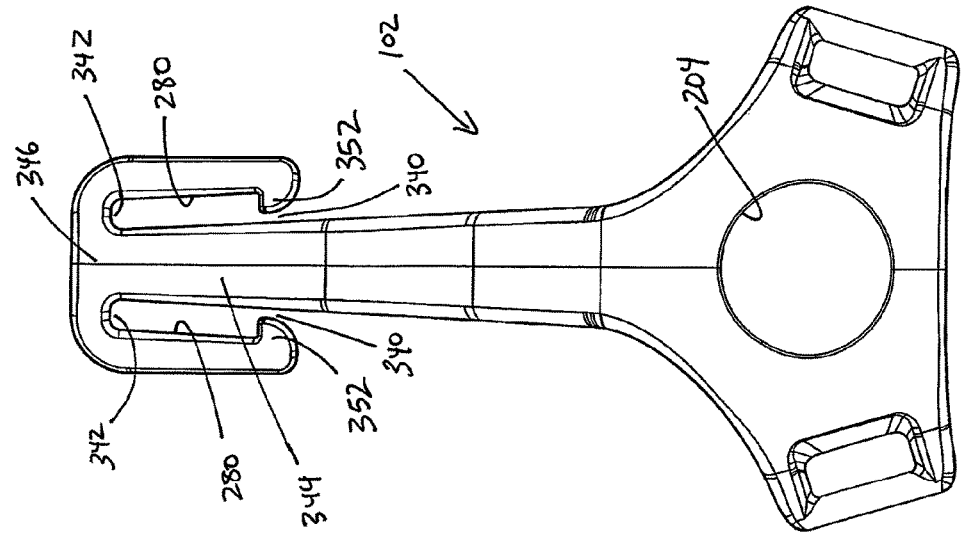
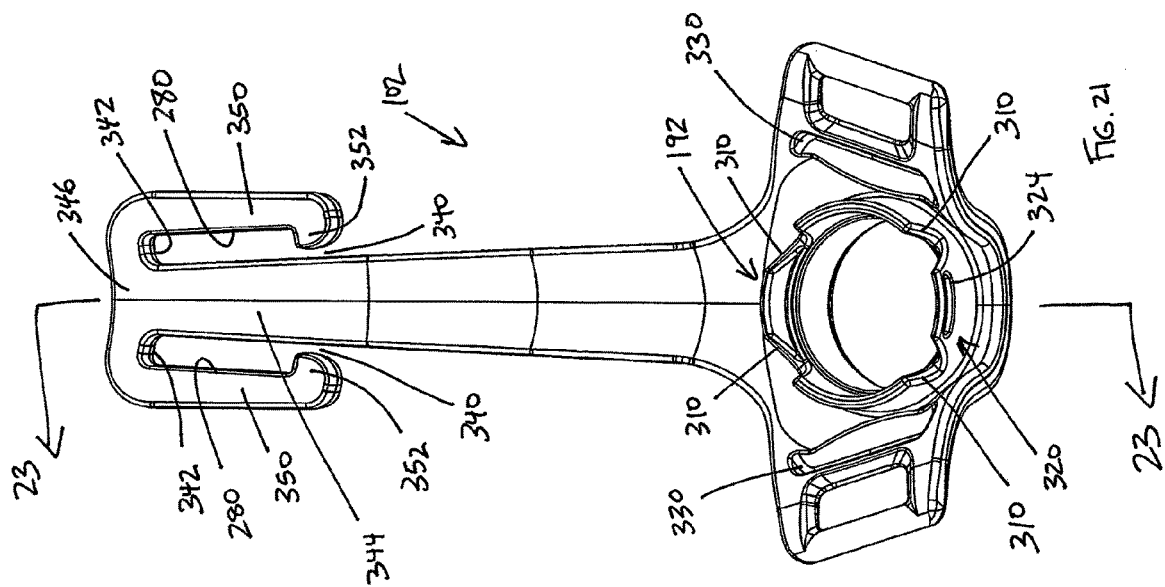

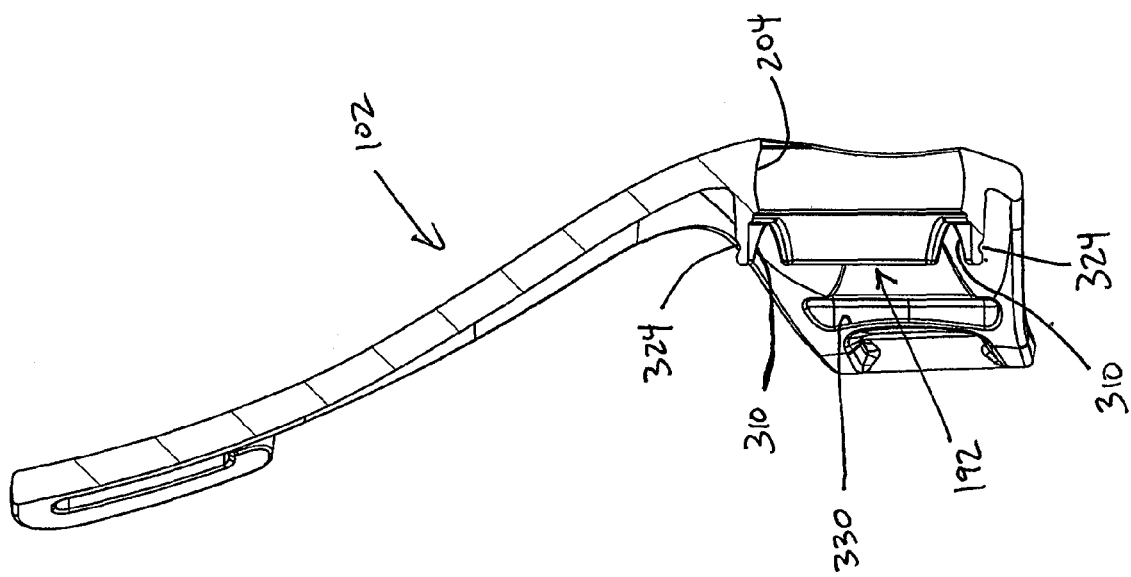

NASAL MASK INTERFACE ASSEMBLY

BACKGROUND OF THE INVENTION

Field of the Invention

The present inventions generally relate to interface assemblies for positive pressure therapy. More specifically, the present inventions relate to nasal mask interface assemblies and headgear.

Description of the Related Art

Interfaces can be used to provide respiratory gases to a user under positive pressure. In configurations in which a nose of a user is covered, the nasal mask typically will overlie a bridge of the nose. Generally, a single seal will circumscribe a portion of the nose of the user.

Such nasal masks commonly are secured to a head of the user with headgear having a t-piece frame that connects to the seal member. In order to sufficiently reduce leakage, the headgear typically is tightened, which results in an elevated pressure being exerted on a bridge of a user's nose. In other words, as the headgear is tightened, the silicone seal typically applies a progressively increasing load on the bridge of the nose. The pressure can be a source of discomfort and, in some circumstances, can lead to pressure sores over time.

SUMMARY OF THE INVENTION

It is an object of the present disclosure to provide one or more constructions and/or methods that will at least go some way towards improving on the above or that will at least provide the public or the medical profession with a useful choice.

In one aspect, a seal member for an interface assembly comprises a face contacting surface. The face contacting surface comprises an edge that at least partially defines an opening. The face contacting surface also comprises a first cheek surface and a second cheek surface. The first cheek surface comprises a first thickened portion and the second cheek surface comprises a second thickened portion.

Preferably, the first and second thickened portions are formed on an interior surface of the seal member.

Preferably, a distal portion of the seal member is overmoulded onto a clip member. Preferably, the clip comprises a feature that receives a complementary feature of an interface frame. Preferably, the clip member tapers in a distal direction.

In one aspect, a seal member for an interface assembly comprises a face contacting surface. The face contacting surface comprises an edge that at least partially defines an opening. The face contacting surface also comprises an upper lip contacting surface, a first cheek surface and a second cheek surface. A sidewall extends distally of the face contacting surface. The sidewall comprises a first lower corner proximate a transition from the upper lip surface to the first cheek surface. The sidewall comprises a second lower corner proximate a transition from the upper lip surface to the second cheek surface. The first lower corner and the second lower corner have a thicker cross-section compared to portions of the sidewall located vertically above the first lower corner and the second lower corner.

Preferably, a distal portion of the seal member is overmoulded onto a clip member. Preferably, the clip comprises a feature that receives a complementary feature of an interface frame. Preferably, the clip member tapers in a distal direction.

In one aspect, a seal member for an interface assembly comprises a face contacting surface. The face contacting surface comprises an edge that at least partially defines an opening. The face contacting surface also comprises an upper lip contacting surface, a first cheek surface and a second cheek surface. A sidewall extends distally of the face contacting surface. The sidewall comprises a first thickened band extending along a portion corresponding to the first cheek surface and a second thickened band extending along a portion corresponding to the second cheek surface.

Preferably, a distal portion of the seal member is overmoulded onto a clip member. Preferably, the clip comprises a feature that receives a complementary feature of an interface frame. Preferably, the clip member tapers in a distal direction.

Preferably, the sidewall of the seal member has a thicker cross section distal of the first and second thickened bands relative to a cross section proximal of the first and second thickened bands.

Preferably, a distal portion of the seal member is overmoulded onto a clip member. Preferably, the clip comprises a feature that receives a complementary feature of an interface frame. Preferably, the clip member tapers in a distal direction.

In one aspect, headgear for an interface assembly comprises a body. A first lower strap and a second lower strap extend away from the body. A first upper strap and a second upper strap extend away from the body. The first lower strap comprises a first lower strap centerline. The second lower strap comprises a second lower strap centerline. A first upper strap comprises a first upper strap centerline. The first and second lower strap centerlines intersect each other before intersecting the first upper strap centerline.

Preferably, the second upper strap comprises a second upper strap centerline and the first upper strap centerline corresponds to the second upper strap centerline.

Preferably, an intersection of the first lower strap centerline and the second lower strap centerline is offset from the first upper strap centerline by a distance of about 23 mm.

Preferably, the first lower strap centerline intersects the first upper strap centerline at a location about 43 mm from a location where the second lower strap centerline intersects the first upper strap centerline.

Preferably, the first upper strap centerline and a second upper strap centerline correlate to each other and do not intersect the entire body of the headgear.

Preferably, the first lower strap centerline extends at an angle relative to the first upper strap centerline with the angle being between about 20 degrees and about 50 degrees.

In one aspect, an elbow for use with an interface assembly comprises a body having a proximal end and a distal end. The proximal end and the distal end are at an angle relative to each other and a bend is defined at a transition from the proximal end to the distal end. The bend comprises a plurality of exhaust holes. The plurality of exhaust holes are integrally formed with the body of the elbow.

In one aspect, an elbow for use with an interface assembly comprises a body having a proximal end and a distal end. The proximal end and the distal end are at an angle relative to each other and a bend is defined at a transition from the proximal end to the distal end. The bend comprises a plurality of exhaust holes. One or more of the exhaust holes comprises a conical first portion and trumpet shaped second portion.

Preferably, the conical first portion is an inner portion and the trumpet shaped second portion is an outer portion.

Preferably, the exhaust holes are integrally formed in the body.

In one aspect, an interface assembly comprises a frame with a seal removably connected to the frame. The seal is configured in accordance with any described and/or shown herein.

In one aspect, an interface assembly comprises a frame with headgear removably connected to the frame. The headgear is configured in accordance with any described and/or shown herein.

In one aspect, an interface assembly comprises a frame with a conduit connector being connected to the frame. The conduit connector comprises an elbow that is configured in accordance with any described and/or shown herein.

In one aspect, an interface assembly comprises a frame with a seal and headgear removably connected to the frame. The seal is configured in accordance with any described and/or shown herein and the headgear is configured in accordance with any described and/or shown herein.

In one aspect, an interface assembly comprises a frame with a seal connected to the frame and a conduit connector being connected to the frame. The conduit connector comprises an elbow. The seal is configured in accordance with any described and/or shown herein and the elbow is configured in accordance with any described and/or shown herein.

In one aspect, an interface assembly comprises a frame with headgear connected to the frame and a conduit connector connected to the frame. The conduit connector comprises an elbow. The headgear is configured in accordance with any described and/or shown herein and the elbow is configured in accordance with any described and/or shown herein.

In one aspect, an interface assembly comprises a frame with a seal and headgear connected to the frame and a conduit connector connected to the frame. The conduit connector comprises an elbow. The seal is configured in accordance with any described and/or shown herein. The headgear is configured in accordance with any described and/or shown herein. The elbow is configured in accordance with any described and/or shown herein.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages of the present invention will now be described with reference to the drawings of a preferred embodiment, which embodiment is intended to illustrate and not to limit the invention, and in which figures:

FIG. 18 is a sectioned view of the interface assembly of FIG. 17 taken along the line 18-18 in FIG. 17.

FIG. 19 is a sectioned view of the interface assembly of FIG. 17 similar to that of FIG. 18 with the seal and clip assembled to the frame.

FIG. 20 is a sectioned view of the seal and clip of the interface assembly of FIG. 17 taken along the line 20-20 in FIG. 17.

FIG. 21 is a rear view of the frame of the interface assembly of FIG. 17.

FIG. 22 is a front view of the frame of the interface assembly of FIG. 17.

FIG. 23 is a sectioned view of the frame of the interface assembly of FIG. 17 taken along the line 23-23 in FIG. 21.

DETAILED DESCRIPTION OF THE PREFERRED EMBODIMENTS

An interface 20 that is arranged and configured in accordance with certain features, aspects and advantages of the present invention can provide improvements in the delivery of CPAP therapy, for example but without limitation. In particular, the sealing interface 20 may exhibit improved sealing characteristics while limiting pressure applied to a bridge of a nose of a user.

System Overview

It will be appreciated that the interface 20 can be used with any delivery device used in respiratory care generally, including with a ventilator, but the sealing interface 20 will be described with reference to use in a humidified CPAP system. The delivery systems also could be VPAP (Variable Positive Airway Pressure), BiPAP (Bi level Positive Airway Pressure) or any other form suitable for use in respiratory therapy.

It will also be appreciated that various features, aspects and advantages of the patient interface 20, while being described in the context of a nasal mask, can be used with any other interface configuration, including oronasal masks and full face masks sealing around the user's nose and mouth, oral masks sealing around the user's mouth, and nasal pillows or other types of masks sealing under the user's nose, for example but without limitation.

Figure 1:
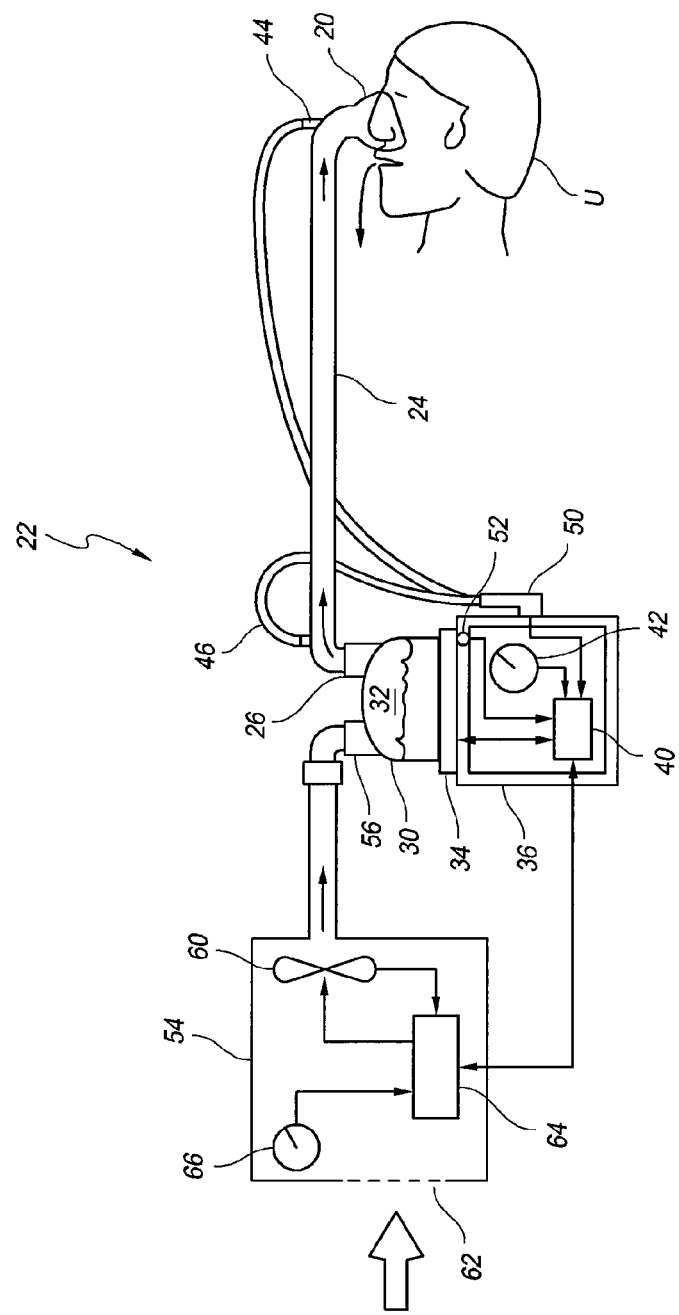
FIG. 1 is a schematic diagram of a system for providing a heated humidified gases stream to a user, such as a continuous positive airway pressure system, as might be used in conjunction with the interface of the preferred and alternative embodiments.

With reference to FIG. 1, a humidified Continuous Positive Airway Pressure (CPAP) system 22 is shown. The illustrated CPAP system 22 provides humidified and pressurized gases to the user U through the interface 20, which is connected to a humidified gases transportation pathway or inspiratory conduit 24.

The inspiratory conduit 24 is connected to an outlet 26 of a humidification chamber 30, which is adapted to contain a volume of water 32. The inspiratory conduit 24 may contain a heating configuration (not shown), such as heater wires, for example but without limitation. The heating configuration can heat the walls of the inspiratory conduit 24 to reduce condensation of humidified gases within the inspiratory conduit 24.

The humidification chamber 30 preferably is formed from a plastics material and may have a highly heat conductive base (e.g., an aluminum base) that is in direct contact with a heater plate 34 of a humidifier 36. The humidifier 36 employs a controller 40 or the like. The controller may comprise a microprocessor-based controller that executes computer software commands stored in an associated memory, for example but without limitation.

The controller 40 receives input commands from multiple sources, including a user input interface 42 (e.g., a dial). The user input interface 42 enables the setting of a predetermined value (e.g., a preset value) of humidity, temperature or other characteristic of the gases supplied to the user U. The controller 40 also may receive input from other sources. For example, temperature and/or flow velocity sensors 44, 46, which are connected through a connector 50 in the illustrated configuration, can communicate with the controller 40. In addition, a heater plate temperature sensor 52 can communicate with the controller.

In response to the user set humidity or temperature value, which can be input via the user interface 42, in combination with other inputs, the controller 40 determines when and/or to what level the heater plate 34 should be energized to suitably heat the water 32 contained within the humidification chamber 30. As the volume of water 32 within the humidification chamber 30 is heated, water vapour begins to fill the volume of the humidification chamber 30 above a surface of the water 32. The water vapour passes out of the outlet 26 of the humidification chamber 30 with a flow of gases (e.g., air) that is provided from a gases supply 54 (e.g., a blower), which enters the humidification chamber 30 through an inlet 56.

The gases supply 54 preferably includes a flow generator 60, which can be a variable speed fan or can include a variable pressure regulator. In the illustrated configuration, the flow generator 60 comprises a variable speed fan. The flow generator 60 preferably draws air or other gases through an inlet 62. The flow generator 60 can be controlled by a controller 64 or can be controlled by the controller 40, for example but without limitation. The controller 64 may control the fan speed, the regulated pressure or the like according to any suitable criteria. For example, the controller 64 may respond to inputs from the controller 40 and a user set value (e.g., a preset value) of pressure and/or fan speed, which can be set with a user interface 66 (e.g., a dial).

Patient Interface

Figure 2:
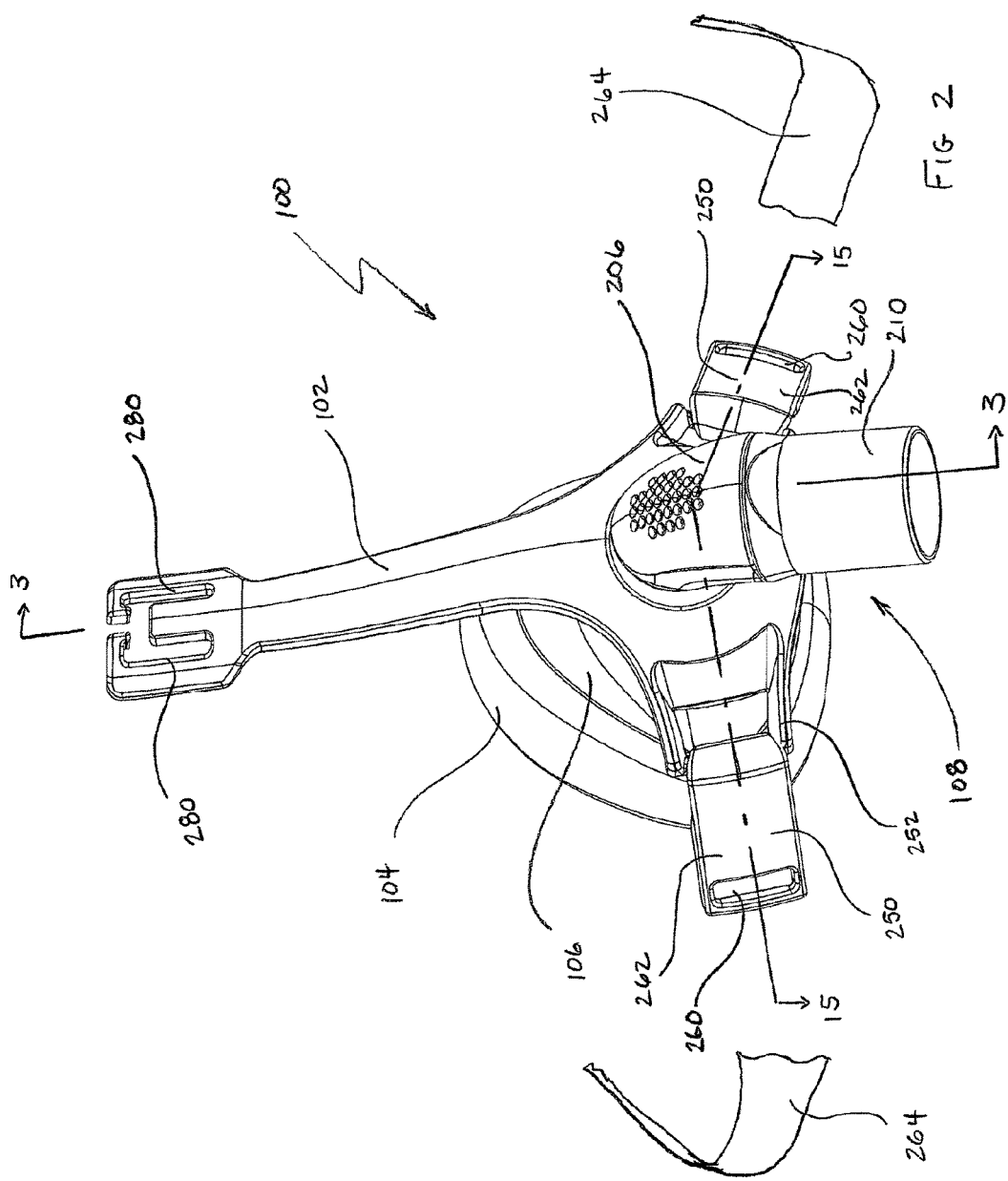
FIG. 2 is a perspective view of an interface assembly that is arranged and configured in accordance with certain features, aspects and advantages of the present invention.
Figure 3:
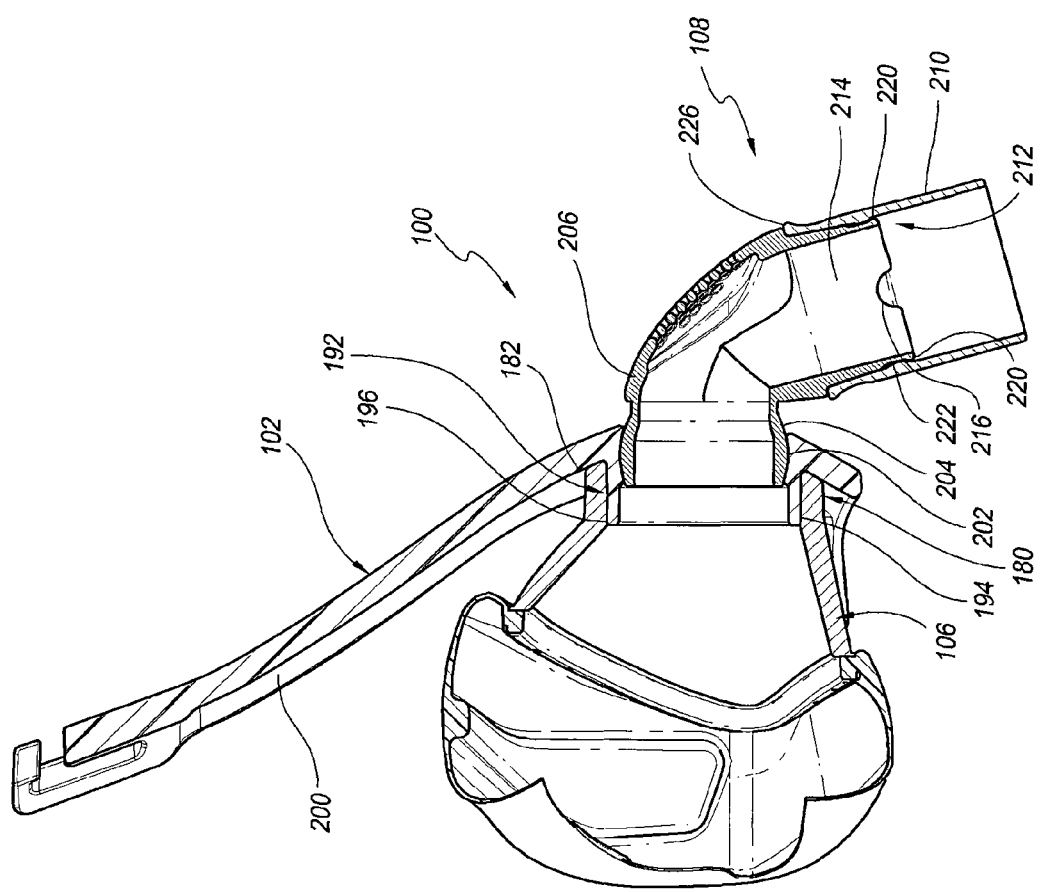
FIG. 3 is sectioned view of the interface assembly taken along the line 3-3 in FIG. 2.

With reference now to FIG. 2 and FIG. 3, the interface 20 generally comprises a mask assembly 100. The mask assembly 100 generally comprises a frame 102, a seal 104 and a clip 106 that is used to secure the seal 104 to the frame 102. The mask seal 104 and the clip 106 can be separately formed and secured together or, in some configurations, the mask seal 104 and the clip 106 can be integrated into a single component. In the illustrated configuration, the mask seal 104 is overmoulded onto the mask seal clip 106. A connector 108 connects a breathing conduit (not shown) to the mask frame 102.

Figure 4:
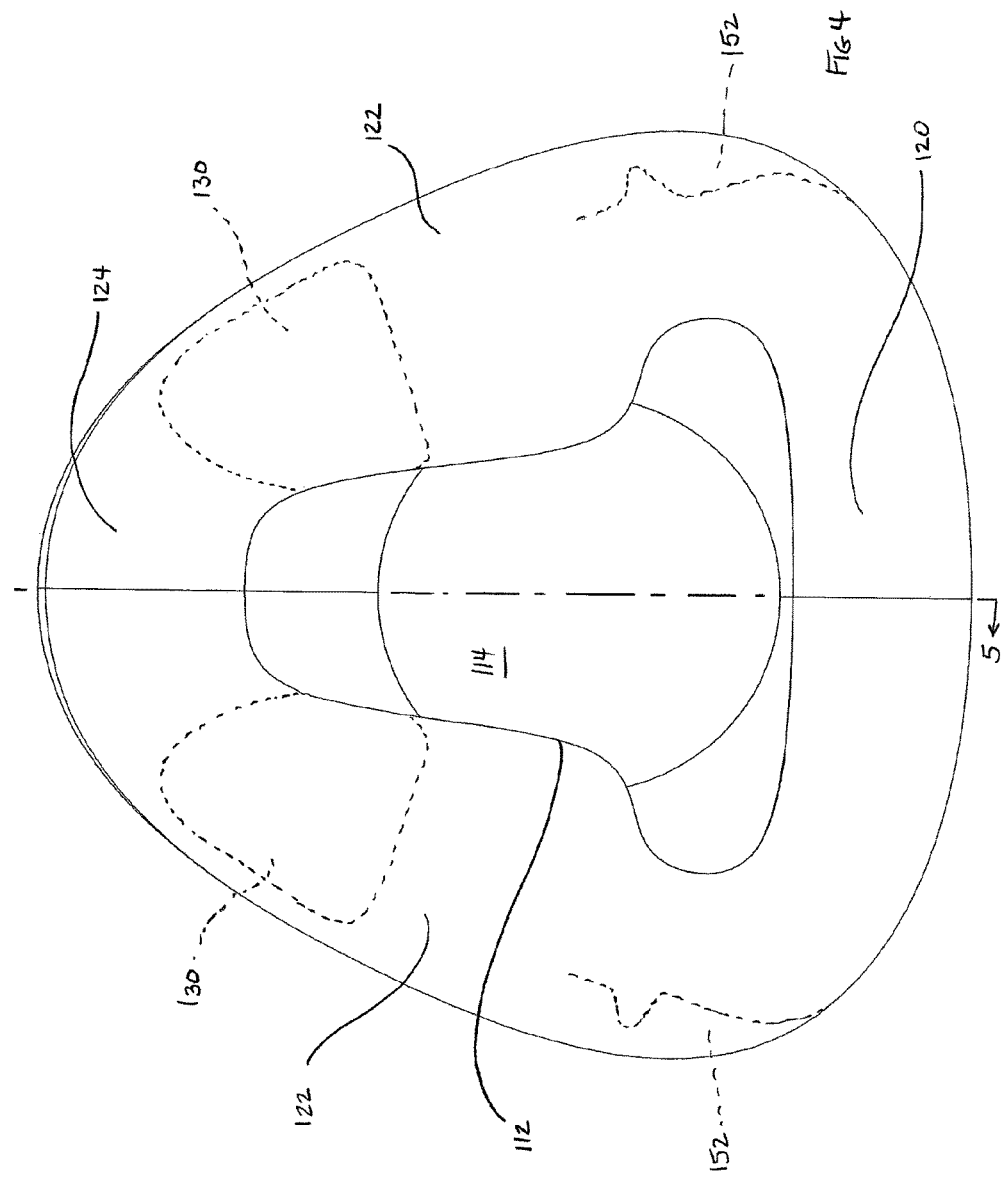
FIG. 4 is a rear view of a seal member and clip of the interface assembly of FIG. 2.

With reference now to FIG. 4, the seal 104 is shown from the rear, which is the surface that bears against a face of the user. The seal 104 comprises a face contacting surface 110. As shown in FIG. 4, the face contacting surface 110 preferably comprises an edge 112 that at least partially defines an opening 114. In the illustrated configuration, the edge 112 surrounds the opening 114. The opening 114 is designed to accommodate at least the lower portion and tip of a nose of the user. Preferably, the opening 114 is generally T-shaped, albeit an inverted T-shape.

The face contacting surface 110 generally comprises a lip surface 120, which is adapted to contact the face of the user at a location above the vermillion border and below the nares. The face contacting surface 110 also comprises two separate cheek surfaces 122, which extend between the lip surface 120 of the face contacting surface 110 and a lateral surface 124 of the face contacting surface 110. The cheek surfaces 122 can contact the medial cheek surface of the user and/or the lateral nose surface of the user. The lateral surface 124 can extend over the nose of the user to connect the two cheek surfaces 122. Other configurations are possible.

Figure 5:
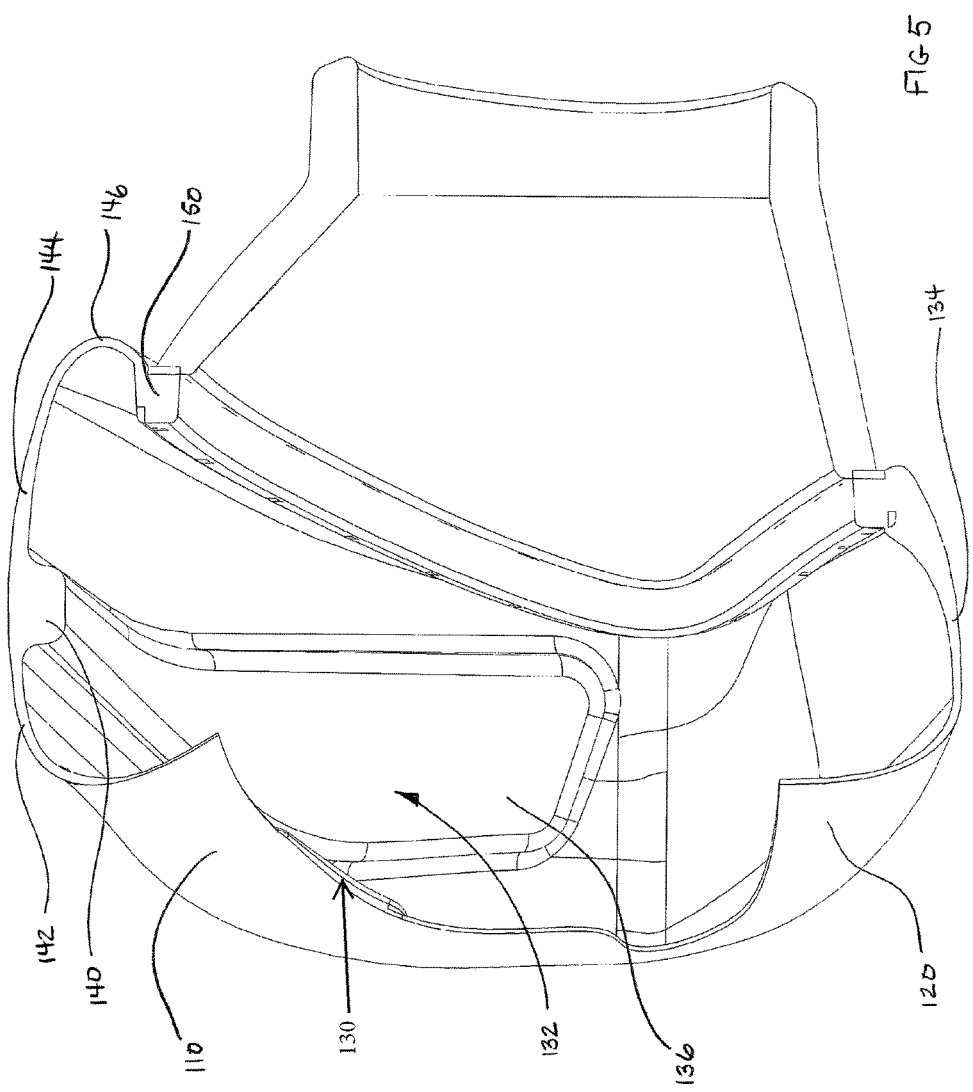
FIG. 5 is sectioned view of the interface assembly taken along the line 5-5 in FIG. 4.

As shown in the sectioned perspective view of FIG. 5, the face contacting surface 110 preferably comprises the thinnest cross section of material in the seal 104. The face contacting surface 110 advantageously can easily deform to substantially seal against the facial contours of the user, including one or more of the upper lip, the medial cheek, the lateral nose and the bridge of the nose. Advantageously, the thin cross section of the face contacting surface 110 over the lips of the user allows for increased stretchability and results in minimal pressure being applied to the region above the lips of the user. The seal 104 can have any suitable configuration. In the illustrated embodiment, the seal 104 is an inflating type. As such, the pressure contained within the seal 104 can urge the face contacting surface 110 against the face of the user.

With reference again to FIG. 4, the illustrated seal 104 also comprises two thickening panels 130, which are shown in hidden lines. The panels 130 generally are positioned along upper portions of the cheek surfaces 122, close to a transition from the cheek surfaces 122 to the lateral surface 124. The panels 130 can be formed on an interior surface of the seal 104. The panels 130 represent locally thickened regions that have been found to enhance the sealing capability of the seal 104. It presently is believed that the panels 130 increase a lateral pressure against the lateral nose surface of the user, which allows pressure from the seal 104 to better contour to the shape of the nose of the user. In other words, the panels 130 may cause a pinching effect on the lateral sides of the nose of the user to allow the pressure from the seal 104 to better contour to the shape of the nose of the user.

Figure 6:
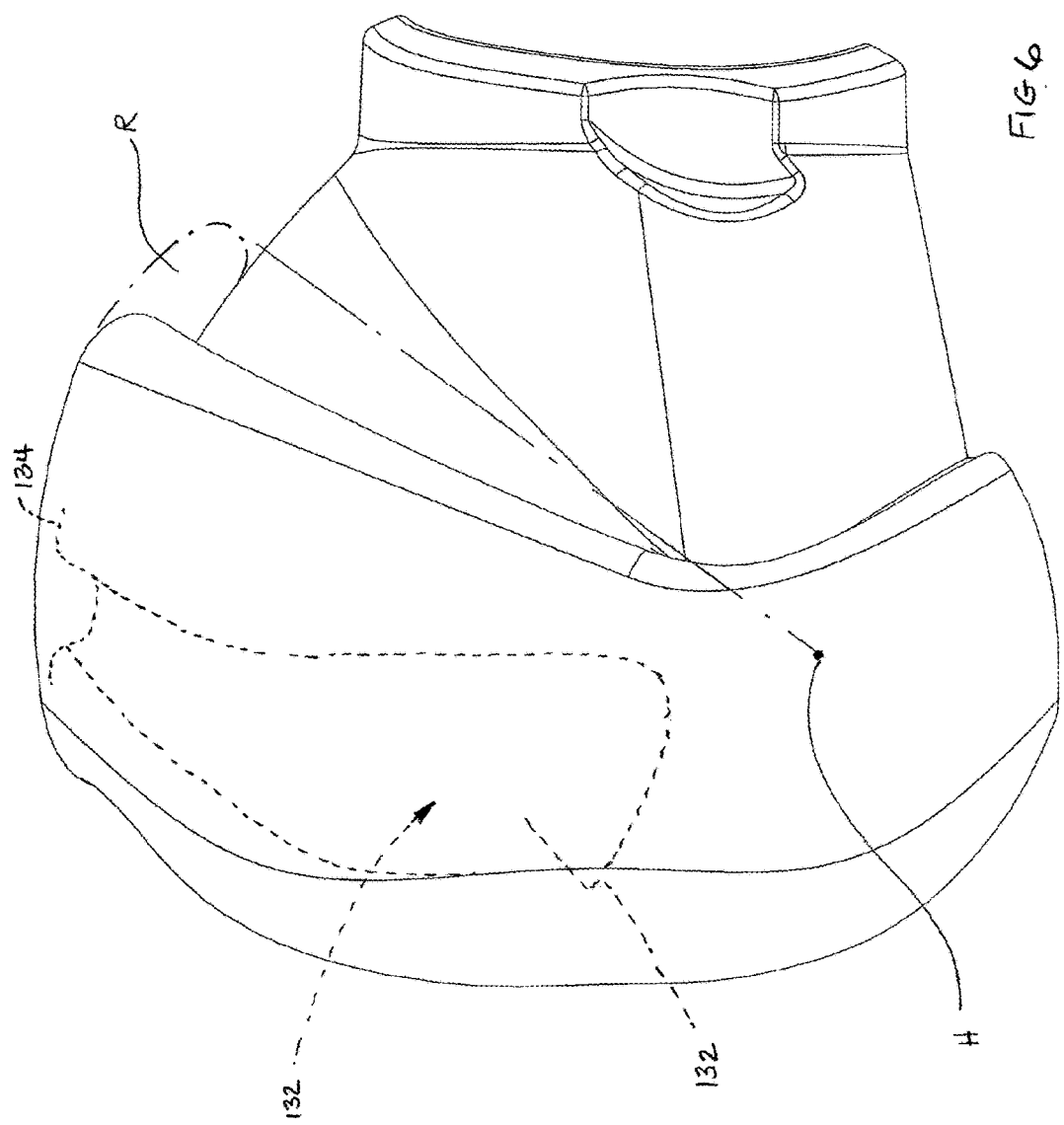
FIG. 6 is a side elevation view of the seal member and clip of FIG. 4 with a thickened portion shown in dashed lines and a rolling action of the seal member shown in dash-dot lines.

With reference to FIG. 5 and FIG. 6, the inside surface of the seal 104 further comprises at least one thickened band 132. While a single thickened band 132 is shown in FIG. 5 and FIG. 6, in some configurations, two or more thickened bands or thickened regions can be provided keeping in mind a desire to achieve the characteristics provided by the thickened band 132.

The illustrated thickened band 132 is positioned along a sidewall 134 of the seal 104. The sidewall 134 extends forwardly from the face contacting surface 110. The band 132 preferably comprises a larger lower region 136 on an inside of each lateral side of the seal 104 and a thinner connecting rib 140 that extends between the lower regions 136 by wrapping around the upper portion of the inside of the seal 104. When the seal 104 receives pressure from the system 22, the thickened band 132 helps to reduce the likelihood of, and/or the degree of, the sidewall 134 ballooning outward. Ballooning outward of the sidewall 134 can cause undesired changes in a shape of the seal 104, which can adversely impact performance of the seal 104.

With reference to FIG. 5, the sidewall 134 preferably comprises a thin walled proximal portion 142 (i.e., close to the face of the user) and a thin wall distal portion 144 (i.e., away from the face of the user). The thin walled proximal portion 142 is connected to the thin walled distal portion 144 with the thickened band 132. Preferably, the face contacting surface 110 forms a flange that curls inward from the thin walled proximal portion 142. More preferably, the face contacting surface 110 tapers away from the proximal portion 142 of the sidewall 134.

With reference to FIG. 5 still, the distal portion 144 curls inward toward the clip 106 at a shoulder 146. In some configurations, the distal portion 144 curls inward toward a rim 150 at the shoulder 146. In the illustrated configuration, the rim 150 is overmoulded with a portion of the clip 106.

The shoulder combined with the thin wall distal portion 144 and the thickened band 132 allows the seal 104 to exhibit a rolling action similar to that disclosed in U.S. Provisional Patent Application Nos. 61/476,188, filed on Apr. 15, 2011, 61/504,295, filed on Jul. 4, 2011, 61/553,067, filed on Oct. 28, 2011, 61/553,872, filed on Oct. 31, 2011 and International Patent Application No. PCT/M2012/000858, filed on Apr. 13, 2012, the entireties of which are hereby incorporated by reference herein. The rolling action is represented rather schematically in FIG. 6 by the dash-dot line and indicated by reference letter R. The distal portion of the seal 104 can pivot about a hinge point H while the distal most portion will roll over itself in the region of the shoulder, as indicated by the rolled portion R shown in dash-dot line in FIG. 6.

The thin wall distal portion 144 and the tighter radius of the shoulder 146 helps to cause a controlled buckling and rolling of the seal 104. In addition, when under pressure from the system 22, the internal pressure facilitates the rolling action by reducing the likelihood of the seal sticking upon itself in the rolling region. Moreover, the stiffened band 132 extends downward toward the hinge point H but need not extend below the hinge point H. The stiffened band 132 also acts as a limit to the degree to which the distal portion 144 can roll and deform. Thus, the distal portion 144 can only roll until the thickened band 132 abuts the rim 150.

In addition, by positioning the thin walled proximal portion 142 between the stiffened band 132 and the face contacting surface 110, the thin walled proximal portion 142 can deform slightly during donning of the mask assembly 100. Preferably, the thin walled proximal portion 142 may deform to some degree before the distal portion 144. The rolling effect provides an enhanced comfort level for the user. Advantageously, the rolling effect allows the shape of the seal 104 to change to accommodate a wide range of nasal bridge heights while maintaining minimal changes to load.

Figure 7:
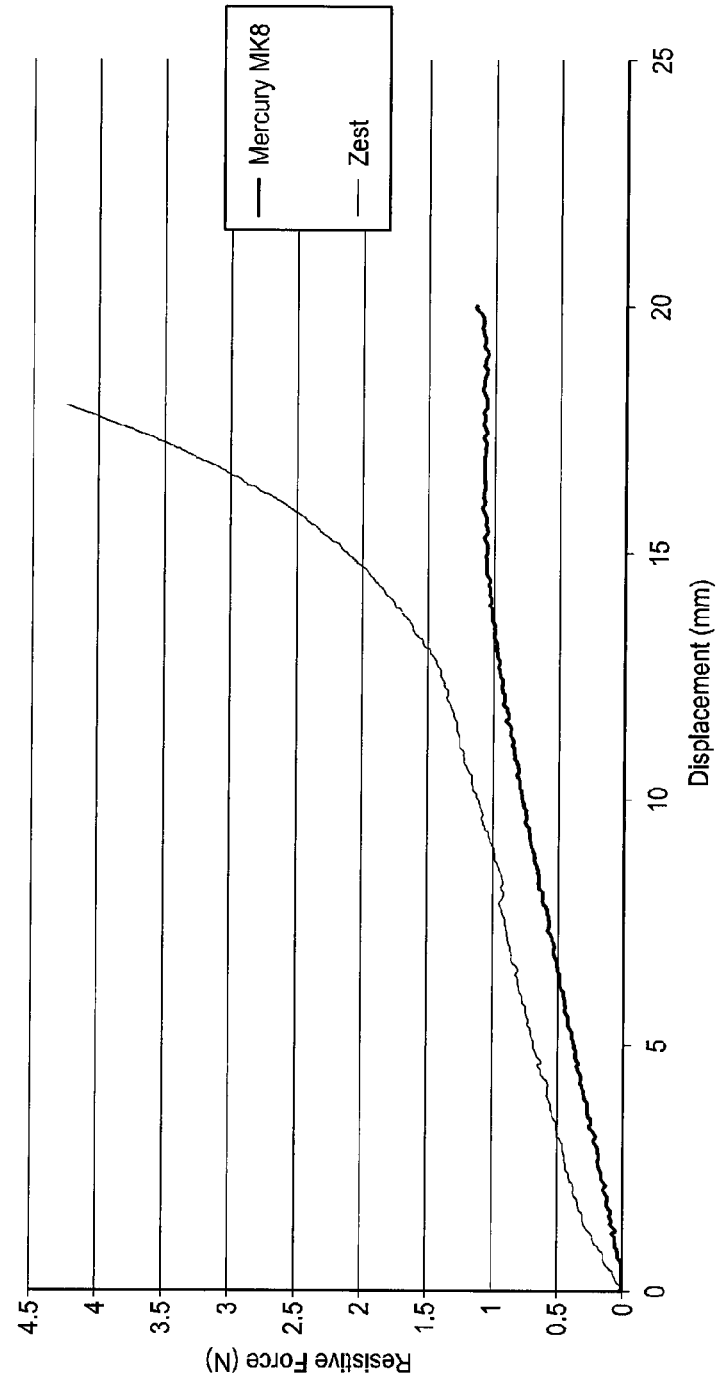
FIG. 7 is a graphical representation of resistance as a function of displacement.

With reference to FIG. 7, a graphical depiction is provided of test data showing a difference provided by the rolling effect. Two masks, a prior art nasal mask sold by Fisher & Paykel Healthcare under the trademark Zest™ was compared to a prototype mask having a rolling effect. Deformation of the masks in the nose bridge region was shown as a function of the force required to create the deformation. As illustrated, over a full range of deformation, the prototype mask remained well below 1.5 N while the prior art mask exceeded 4 N of force over the same range of deformation. Moreover, as shown in FIG. 7, at all distances of deformation, the prototype mask was well below the prior art mask. Thus, the total force from no displacement to full displacement of the prototype mask was about 1 N. Moreover, the increase in force experienced over the final 7 mm (e.g., 13 mm to 20 mm displacement) of displacement was less than about 0.3 N.

With reference to FIGS. 17-23, an alternative embodiment of an interface assembly 100 includes a seal 104 having at least one lower thickened band 300 in addition or alternative to the thickened band 132. With the exception of the at least one lower thickened band 300 and other features described below, the interface assembly 100 of FIGS. 17-23 is the same as or similar to the interface assembly 100 of FIGS. 2-16. Therefore, the same reference numbers are used to denote the same or corresponding components or features in both embodiments. With particular reference to FIG. 20, preferably, lower thickened band 300 is provided in addition to the thickened band 132. The lower thickened band 300 is located within a lower portion of the seal 104 and, preferably, within a lower half of the seal 104 and/or below the thickened band 132. The thickened band 300 is positioned along a lower portion of the sidewall 134 of the seal 104 and preferably is generally or substantially aligned in a fore-aft direction with the thickened band 132. However, in other arrangements, the bands 132, 300 could be offset from one another in the fore-aft direction. In other alternative arrangements, a portion or all of the thickened bands 132 and/or 300 could be arranged generally or substantially in a horizontal plane when the seal 104 is in an upright position (oriented as in FIG. 20). In some such arrangements, one or more thickened bands 132 and/or 300 could extend generally or substantially in a lateral direction of the seal 104. For example, a single thickened band 132 or 300 could be provided, which, in some arrangements, could be generally or substantially at a mid-line of the seal 104. Alternatively, two or more thickened bands 132 or 300 could be provided, which, for example, could be spaced above and below a mid-line of the seal 104. Furthermore, a combination of one or more generally or substantially lateral bands and one or more generally or substantially vertical or circumferential bands could be provided.

The illustrated band 300 preferably comprises a larger upper region 302 on an inside of each lateral side of the seal 104 and a thinner connecting rib 304 that extend between the larger upper regions 302. The upper regions 302 and/or the connecting rib 304 preferably are generally similar in shape to the lower region 136 and rib 140 of the band 132. However, in the illustrated arrangement, the band 300 is scaled down to a somewhat smaller size than the band 132 to correspond to the lower portion of the seal 104 being somewhat thinner (in a fore-aft direction) than an upper portion of the seal 104. Preferably, the band 300 performs a substantially similar or identical function to the band 132. For example, the band 300 preferably reduces the likelihood and/or degree of the sidewall 134 ballooning outward and allows a lower portion of the seal 104 to exhibit a rolling action in a manner similar or identical to that described above with respect to the band 132.

Figure 8:
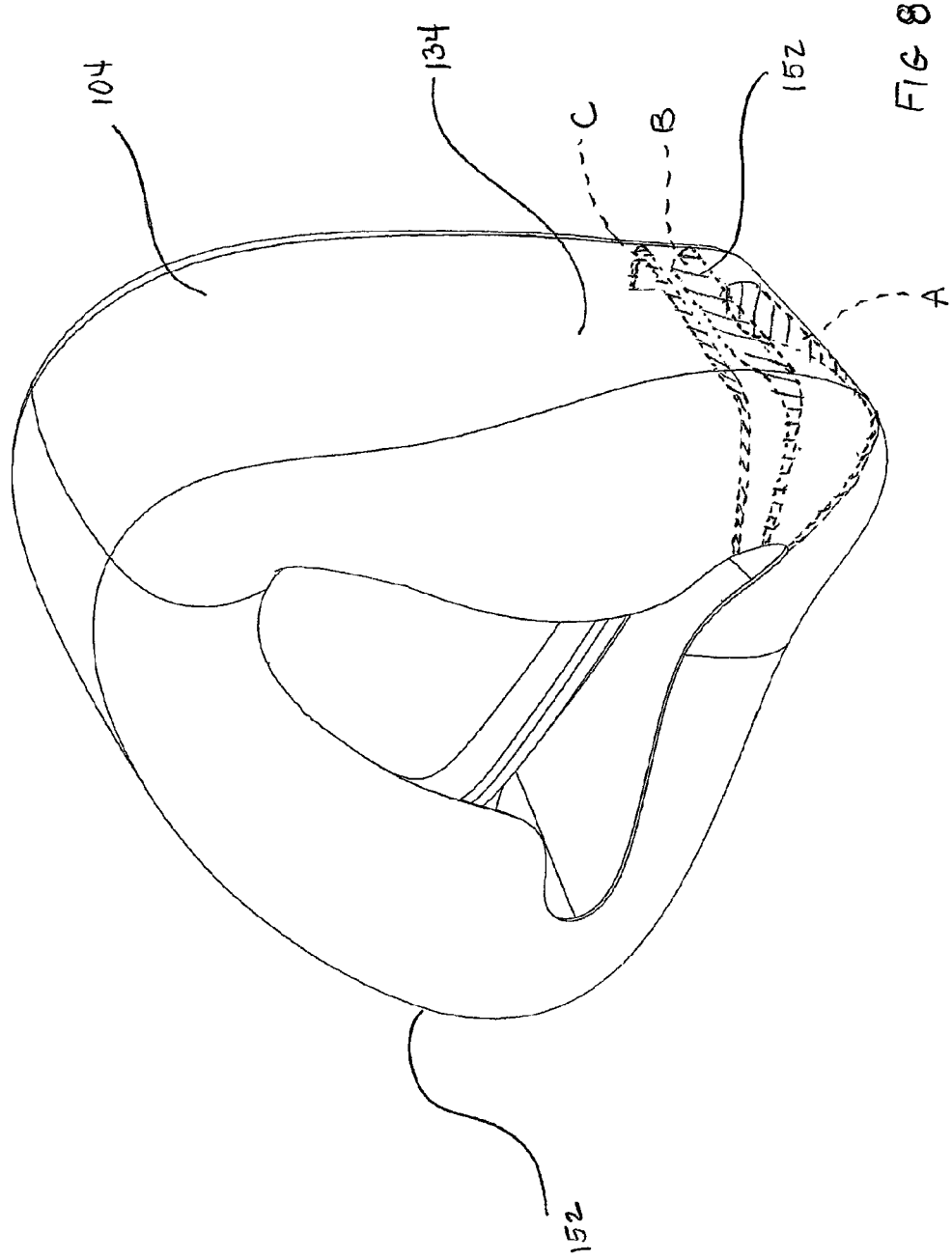
FIG. 8 is a perspective view of a seal member with three different sections shown in hatched areas.

With reference now to FIG. 8, three different cross sections are illustrated on a lower right portion of the illustrated seal 104. A lower most cross section, which is proximate to a corner of the illustrated seal 104, carries reference letter A. A slightly higher cross section carries reference letter B and an even higher cross section carries reference letter C. As illustrated, the intermediate cross section B is substantially thicker than the two adjacent cross sections A, C. Although the three cross sections A, B, C are relatively close together, the wide differences in thickness results in the ability to create localized loading against the face of the user.

It presently is believed that the face of the user can tolerate more loads or pressure in certain regions compared to other regions. By increasing the thickness of the side wall 134, forces can be better transmitted through the sidewall 134 from the clip 106 to the face contacting surface 110. Similarly, reduced thicknesses in the side wall 134 results in less force being transmitted between the clip 106 and the face contacting surface 110 through the side wall. In some configurations, it is believed that the face of the user can better tolerate pressure in the region of the maxilla, just below the zygomatic progress. For this reason, the lower corner regions 152 comprise a region of increased thickness (e.g., section B). When coupled with a forehead contact point provided by the frame 102, a triangle support can be defined among the two lower regions 152 of the seal 104 and the forehead contact point. The triangular support provides a stable platform on the face that can help resist dislodging during use.

Figure 9:
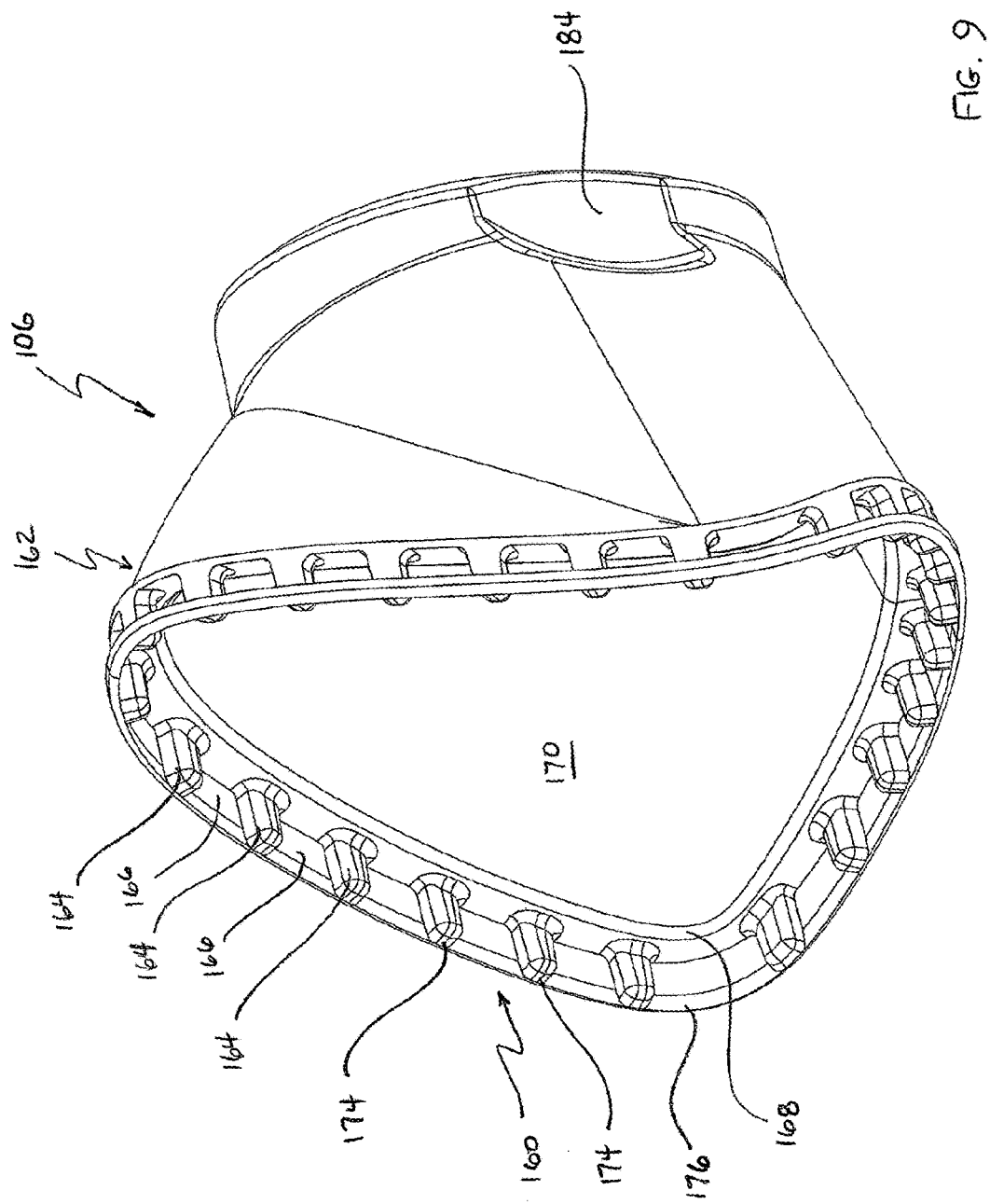
FIG. 9 is a perspective view of the clip of FIG. 4.

To permanently attach the seal 104 to the clip 106, overmolding can be used. With reference to FIG. 9, the clip 106 is shown without the seal 104 attached. The clip 106 can be formed of any suitable rigid or semirigid material. In one configuration, the clip 106 is formed from a polycarbonate material. Because the seal 104 preferably is formed from a silicone material and because the clip 106 is formed from a polycarbonate material, a retention structure 160 has been provided on the clip 106 to allow the seal 104 to be secured overmoulded onto the clip 106. In other words, the silicone material of the seal 104 generally does not adhere to the polycarbonate material of the clip 106 so the seal 104 is retained on the clip 106 by positively locking the silicone material around features of the retention structure 160.

The retention structure 160 of the clip 106 is formed at a proximal end 162 of the clip 106. While the illustrated retention structure 160 is integrally formed with the clip 106, the two could be separately formed and secured together in any suitable manner. The integrated construction, however, provides improved manufacturability and a more durable finished product.

The retention structure 160 comprises a plurality of posts 164 that define a plurality of slots 166. Preferably, the posts 164 are spaced about a peripheral surface 168 that defines an opening 170 at the proximal end of the clip 106. More preferably, the posts 164 are substantially equally spaced about the peripheral surface 168. Even more preferably, the posts 164 are spaced about the peripheral surface 168 such that a ratio of approximately 1:2 is defined between the posts 164 and the intervening slots 166. The 1:2 ratio has been found to maximize a strength of connection between the seal 104 and the clip 106.

Figure 10:
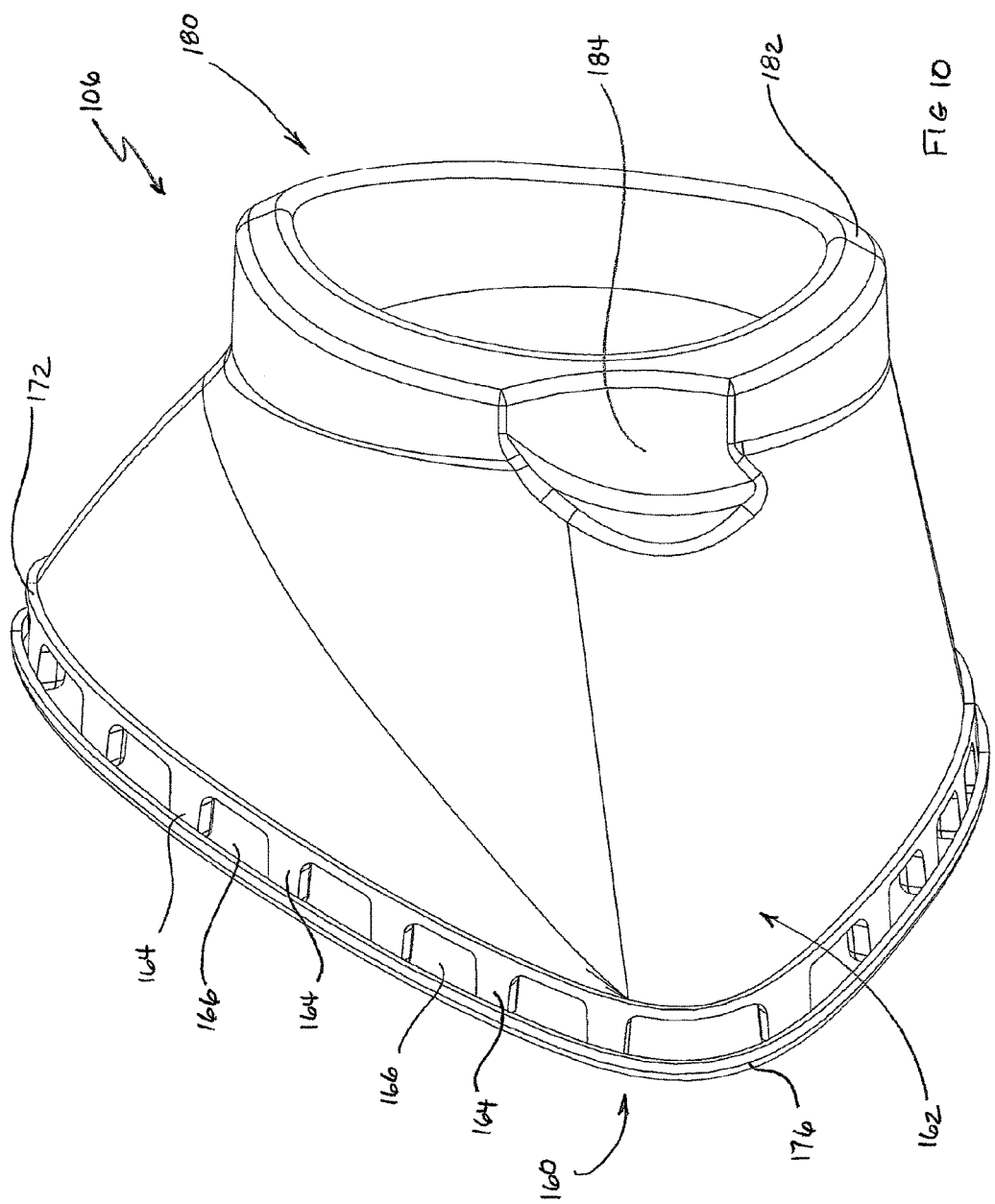
FIG. 10 is another perspective view of the clip of FIG. 4.

With continued reference to FIG. 9 and FIG. 10, the retention structure 160 preferably comprises at least one distal surface 172 and at least one proximal surface 174 that are generally parallel to each other. In the illustrated configuration, the at least one distal surface 172 comprises a ring-like surface that encircles the proximal end 162 of the clip 106 while the at least one proximal surface 174 comprises a plurality of ends of the posts 164. The parallel surfaces 172, 174 help to minimize compression and resulting distortion from the clamp forces experienced during the overmoulding process.

Moreover, as shown in FIG. 9 and FIG. 10, the slots 166 generally are enclosed by a ring 176. In the illustrated configuration, the ring 176 encircles an outside of the posts 164 at the distal end of the posts 164. Other configurations also may be possible. The illustrated construction, however, provides a simple to manufacture construction.

With reference to FIG. 10, a distal end 180 of the clip 106 is configured to mount to the frame 102. Preferably, the clip 106 is easily mounted to the frame 102 and easily removed from the frame 102 such that cleaning of the clip 106 and attached seal 104 can be facilitated. More preferably, the distal portion 180 is adapted to seal with a surface of the frame 102. Even more preferably, a distal surface 182 is adapted to seal against a surface of the frame 102.

With reference still to FIG. 10, the distal portion 180 of the clip 106 comprises one or more recesses 184. Preferably, the recesses 184 also are designed to seal against the frame 102. In particular, the low profile frame 102 comprises one or more protrusions 190 that extend rearward toward the clip 106. To provide a close fit and to reduce the profile of the assembly 100, the recesses 184 in the clip 106 advantageously accommodate these protrusions.

Figure 11:
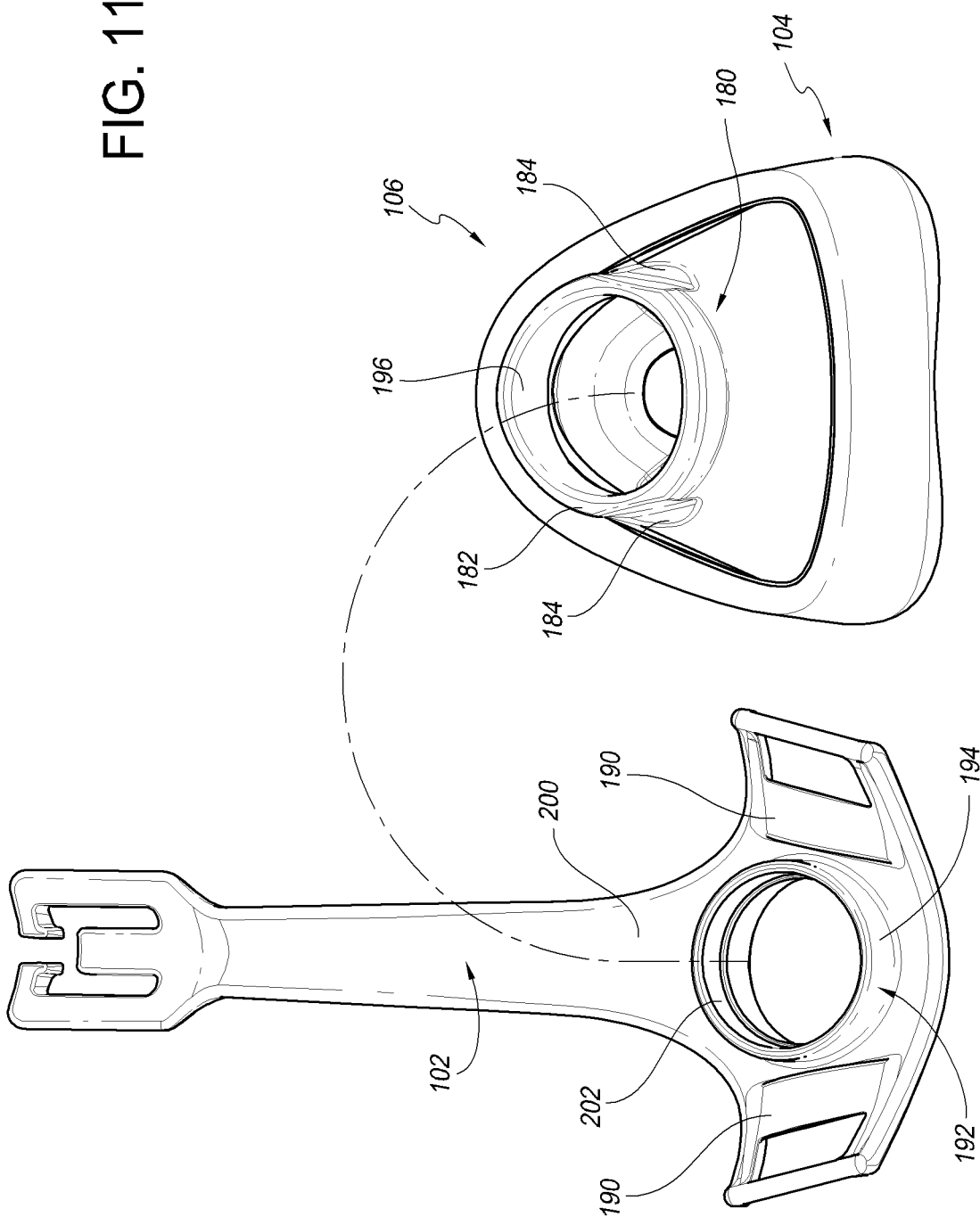
FIG. 11 is a perspective view of the seal member and clip of FIG. 4 and a mask frame of the interface assembly of FIG. 2.

With reference to FIG. 3 and FIG. 11, the frame 102 and the clip 106 preferably connect together in an airtight or sealed relationship. In the illustrated configuration, the frame 102 comprises a mounting boss 192 that extends toward the clip 106. The mounting boss 192 comprises an outer surface 194 over which an inner surface 196 of the distal end 180 of the clip 106 slides. Preferably, the connection between the boss 192 and the distal end 180 of the clip 106 is a taper fit. More preferably, the connection comprises a 1:40 medical taper, which provides a sealing surface to minimize leakage between the two components. Even more preferably, the taper connection comprises an interference fit with 2 mm of travel when measured from a rear face 200 of the frame 102 to the distal surface 182 of the clip 106. While the outer surface 194 of the illustrated boss 192 and the inner surface 196 of the illustrated distal end 180 are generally cylindrical, other shapes are possible.

With reference to FIGS. 17-23, the alternative interface assembly 100 includes a modification of the removable mounting arrangement between the clip 106 and the frame 102. In particular, the mounting boss 192 comprises a wall portion that is intermittent or non-continuous around its circumference. Preferably, a proximal end (i.e., closest to the user) includes at least one and preferably a plurality of recesses or notches 310 that extend toward a distal end of the mounting boss 192 to facilitate the connection of the clip 106 to the frame 102. In particular, the notches 310 allow the wall portions of the boss 192 in between the notches 310 to flex inwardly to effectively reduce the diameter of the mounting boss 192 during assembly of the clip 106 to the frame 102. In the illustrated arrangement, the notches 310 are generally or substantially triangular in shape and four notches 310 are provided. However, other shapes (e.g., generally or substantially rectangular, square, trapezoidal, semicircular) and numbers (e.g., 2, 3, 5, 6 or more) of notches 301 can be used. In addition, preferably the notches 310 are spaced unevenly around the circumference of the mounting boss 192. In the illustrated arrangement, the notches 310 are arranged in an upper pair and a lower pair in which the circumferential distances between the individual notches 310 of the upper and lower pairs are less than the circumferential distances between a notch 310 of the upper pair and the adjacent notch 310 of the lower pair. Preferably, in other respects, the mounting boss 192 of the interface assembly 100 of FIGS. 17-23 is similar to the mounting boss 192 of the interface assembly 100 of FIGS. 2-16, including the taper fit, for example.

The clip 106 and frame 102 of FIGS. 17-23 preferably also includes an interference or interlocking arrangement 320 that assists in maintaining the connection between the clip 106 and the frame 102 and/or increases the force required to separate the clip 106 from the frame 102. Such an arrangement desirably reduces the likelihood of unintentional or undesired separation of the clip 106 and frame 102. Preferably, one of the clip 106 and frame 102 comprises at least one protrusion and the other of the clip 106 and frame 102 comprises at least one recess sized and shaped to accommodate the protrusion. In the illustrated arrangement, the clip 106 includes a pair of protrusions 322 and the frame 102 includes a complementary pair of recesses 324; however, this arrangement could also be reversed. Preferably, the protrusions 322 are located on the top and bottom of the inner surface 196 of the distal end 180 of the clip 106 and the recesses 324 are located on the top and bottom of the outer surface 194 of the mounting boss 192 of the frame 102. In the illustrated arrangement, the protrusions 322 and recesses 324 are diametrically opposed from one another and each is elongated in a circumferential direction of the respective surfaces 196 and 194 to maximize the length of the interfering or interlocking surfaces tending to inhibit separation of the frame 102 and clip 106 and minimize the length in the axial direction.

Preferably, the frame 102 of the interface assembly 100 of FIGS. 17-23 includes at least one recess 330 that, in use, accommodates the distal portion 180 of the clip 106. In the illustrated arrangement, the frame 102 includes a pair of recesses 330 that are positioned on opposing sides of the mounting boss 192 and interact with the clip 106 to inhibit or prevent rotation of the clip 106 relative to the frame 102. Preferably, lower ends of the recesses 330 are positioned close to the mounting boss 192 and upper ends of the recesses 330 extend laterally outward away from the mounting boss 192. In comparison to the clip 106 of FIGS. 2-16, at least a portion of a circumference of the distal portion 180 of the clip 106 of FIGS. 17-23 has a smaller wall thickness. The clip 106 of FIGS. 17-23 transitions to a larger wall thickness portion at a shoulder 332, which defines a distally-facing surface 334. Preferably, the surface 334 contacts an end surface 336 of the recesses 330 in addition to the distal surface 182 contacting the frame 102, as illustrated in FIG. 19, to assist in creating a seal between the clip 106 and the frame 102. In addition, the contact between the surface 334 and the end surface 336 can define a completely connected position between the clip 106 and the frame 102. The shoulders 332 can be defined by the recesses 184 of the clip 106 and, thus, can be coextensive with the recesses 184. Engagement of the recesses 184 and the recesses 330 can inhibit or prevent rotation of the clip 106 relative to the frame 102. In other arrangements, the shoulders 332 could circumscribe a greater distance than the recesses 184 or a single shoulder 332 could circumscribe the entire distal portion 180.

With reference to FIG. 3 and FIG. 11, the boss 192 preferably surrounds an inner surface 202 that defines a socket for a ball connection 204 to the connector 108. In the illustrated configuration, the connector 108 generally comprises an elbow 206 and a swivel 210. The swivel 210 can be used to connect to the inspiratory conduit 24 or other breathing tube. Preferably, the elbow 206 is connected to the frame 102 with the joint defined by the ball 204 and the socket 202 while the swivel 204 is connected to the elbow with a cantilevered bump configuration 212.

The joint defined by the ball 204 and the socket 202 preferably enables a limited range of pivotal movement. In some configurations, the ball 204 can pivot up to about 30 degrees relative to the socket 202. Other ranges of pivotal movement also can be defined if desired.

In the illustrated configuration, the ball 204 is pressed into the socket 202 of the frame 102 from the side of the frame 102 having the rear face 202. In other words, the elbow 206 is fed through the socket 202 and the ball 204 is pressed into engagement with the socket 202. In such a configuration, the elbow 206 is unlikely to be easily disassembled from the frame 102 by the user.

On the other hand, the swivel 210 is designed to be easily removed from the elbow 206. Preferably, the swivel 210 is fully rotatable about its axis relative to the elbow 206 and the swivel 210 can be removed axially from the elbow 206 with as little as about 30 N of force. Moreover, the connection between the elbow 206 and the swivel 210 preferably is designed to reduce leakage at the connection. In the illustrated configuration, leakage is maintained at less than about 0.05 to about 0.4 L/min at 10 cm $H_2O$.

With reference to FIG. 3, a distal end 214 of the elbow 206 preferably comprises two or more cut out regions or recesses 216. The recesses 216 can have any suitable shape and, in the illustrated configuration, the recesses 216 comprise a semicircular configuration that extends upward into the distal end 214 of the elbow 206. The distal end 214 of the elbow 206 also comprises at least one bump 220, and preferably two or more bumps 220. Preferably, each of the bumps 220 extends around an arc of about 70 degrees. More preferably, each of the bumps 220 is generally centered between two recesses 216 and each of the bumps 220 extends about 70 degrees around an outer surface of the distal end 214 of the elbow 206.

The swivel 210 preferably is generally cylindrical in configuration. As shown in FIG. 3, the swivel 210 has an inwardly extending ridge 222. The ridge 222 preferably encircles the entire inner surface. In some configurations, the ridge 222 can be interrupted. Preferably, however, the ridge 222 does not have any interruptions large enough to accommodate the entire bump 220 such that the ridge 222 and the bump 220 can cooperate to keep the swivel 210 mounted over the distal end 214 of the elbow 206. When assembling the swivel 210 to the elbow 206, the recesses 216 allow the bumps 220 to deflect inward such that the bumps 220 can slide over the ridge 222 and then snap back outward to secure the bumps 220 under the ridge 222. For this reason, the distance from a shoulder 224 (see FIG. 12) to the top of the bump 220 (shown as X in FIG. 12) is substantially equal to or slightly larger than a distance from a proximal end 226 of the swivel (see FIG. 3) to the bottom edge of the ridge 220.

Figure 12:
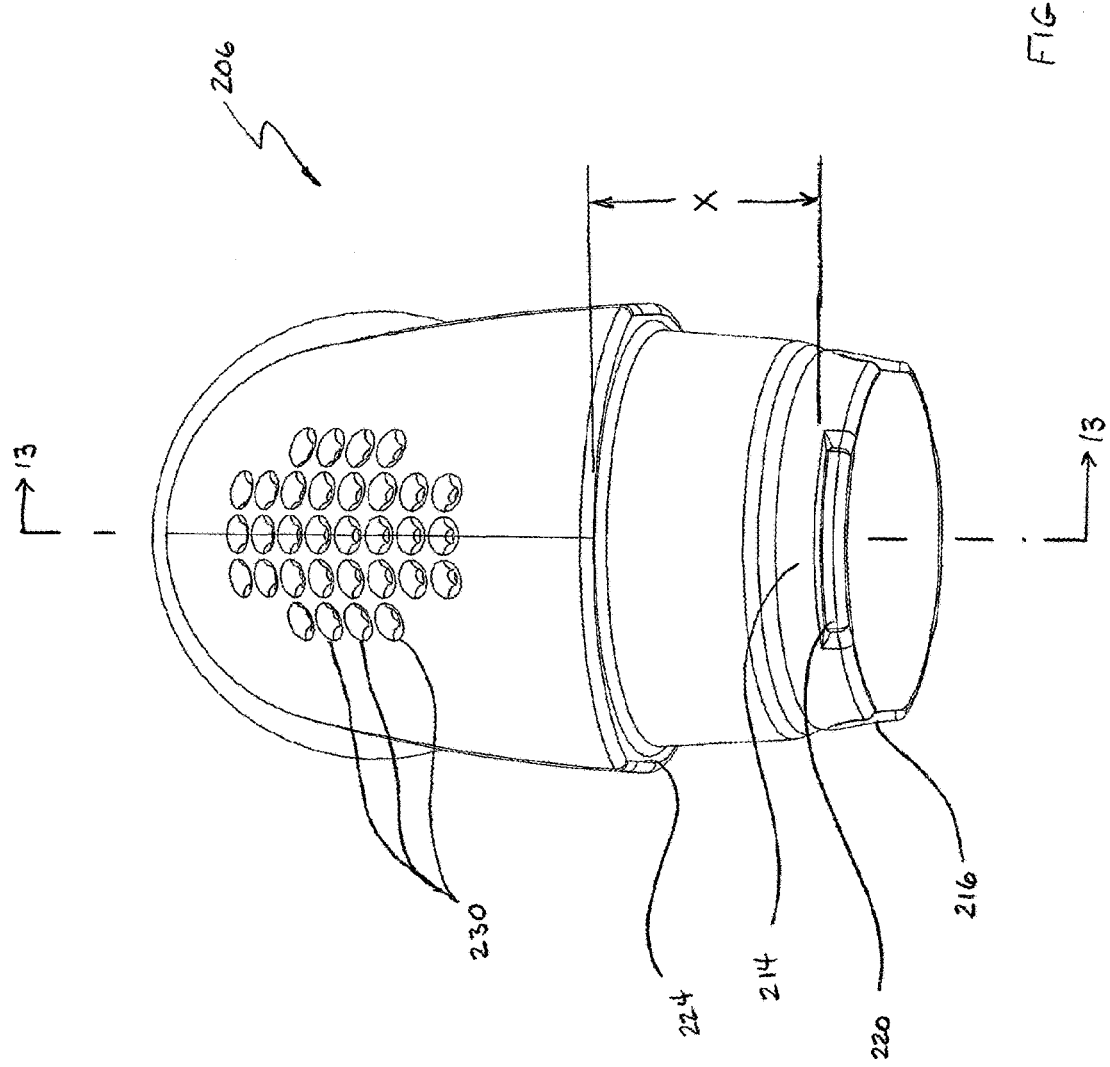
FIG. 12 is a front view of an elbow of the interface assembly of FIG. 2.

With reference now to FIG. 12, the elbow 206 preferably comprises a plurality of integrally formed exhaust holes 230. While the exhaust holes 230 could be formed on a separate insert that is secured to the elbow 206, integrally forming the exhaust holes 230 provides a cleaner aesthetic appearance and provides simplified assembly of the interface assembly 100. The exhaust holes preferably are formed on a surface of the elbow 206 that is on an outside of the turn from the proximal end, which has the ball 204, toward the distal end 214. Other configurations are possible.

Figure 13:
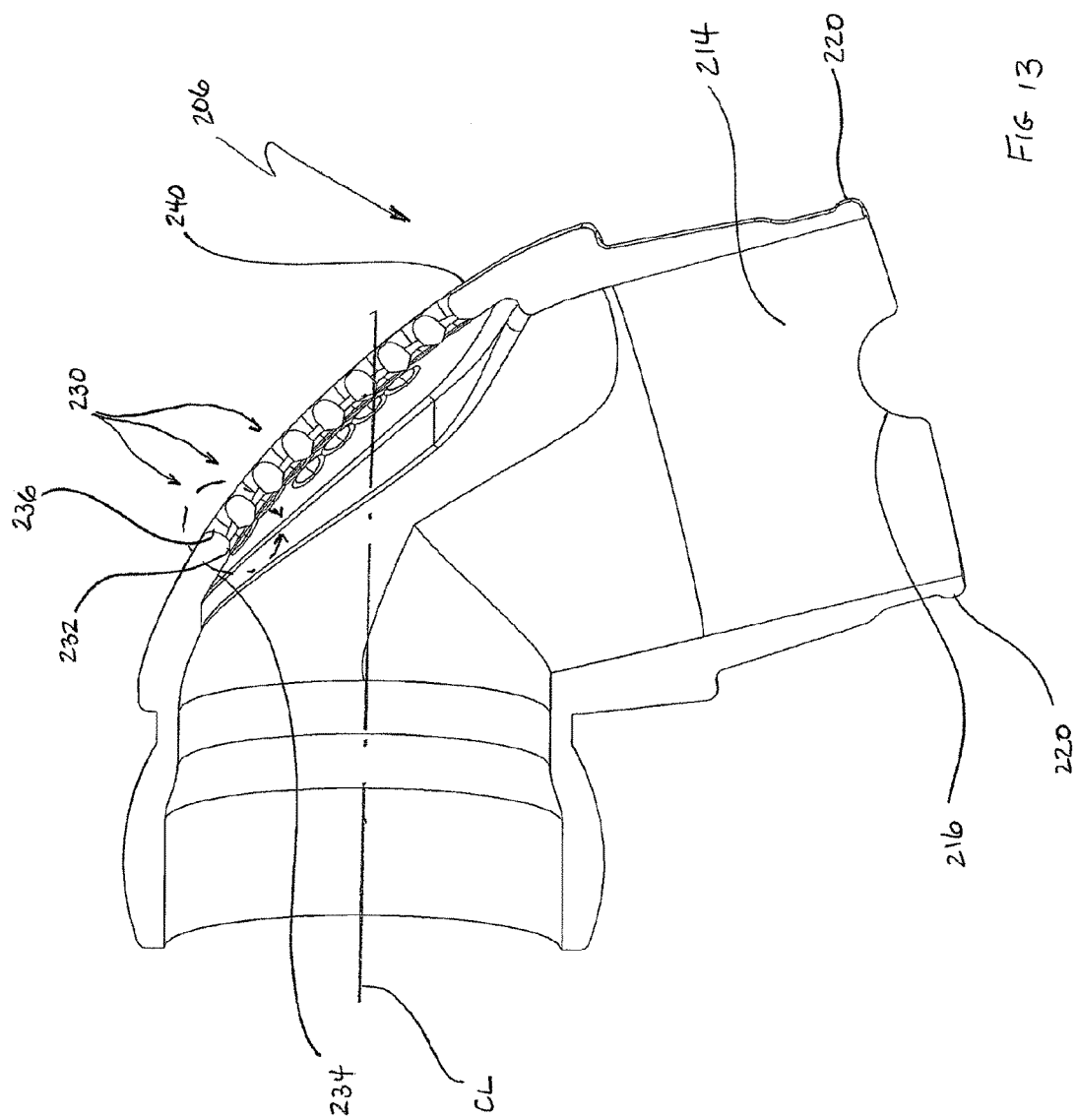
FIG. 13 is a sectioned view of the elbow taken along the line 13-13 in FIG. 12.
Figure 14:
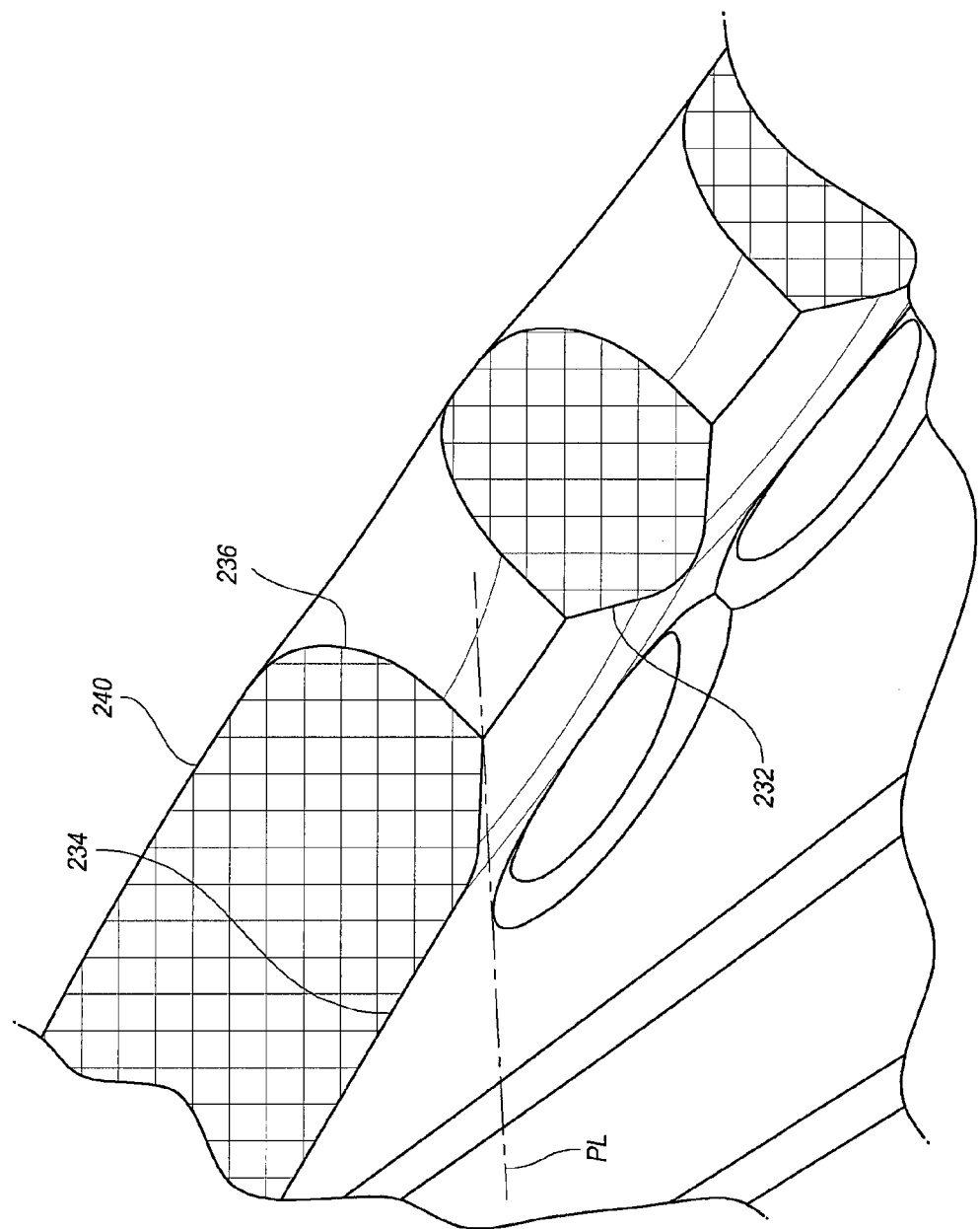
FIG. 14 is an enlarged sectioned view of the elbow taken within the region identified by the line 14-14 in FIG. 13.

With reference to FIG. 13, the exhaust holes 230 preferably comprise a two part configuration. A proximal end 232 of one or more of the exhaust holes 230 forms a conical shaped depression into an inner surface 234. In other words, the proximal end 232 of one or more of the exhaust holes 230 comprises a countersink-shaped surface. A distal end 236 of one or more of the exhaust holes 230 comprises a trumpet-shaped surface. In other words, the distal end of one or more of the exhaust holes 230 comprises a part of an hourglass shape. Preferably, the conical shape of the proximal end 232 and the trumpet shape of the distal end 236 are generally axially aligned and feature a smooth transition between the two shapes. More preferably, all or substantially all of the exhaust holes 230 have this configuration. Even more preferably, the axial centerlines of all or substantially all of the exhaust holes 230 are generally parallel to each other.

With continued reference to FIG. 13, the proximal ends 232 of the exhaust holes 230 preferably define a conical surface that, when viewed in cross section, are substantially parallel to an axial centerline CL of the proximal end of the elbow. In other words, the axial centerline CL generally correlates to a direction of insertion and removal of a die or insert during manufacture. More preferably, when viewed in cross-section, the proximal ends 232 of the exhaust holes have at least one sidewall (when viewed in section) that, when viewed in section, will extend generally parallel to (see reference line PL) or extend generally skewed relative to parallel such that the surface extends away from parallel in moving in a proximal direction (i.e., as the proximal end 232 expands). In this manner, the proximal ends 232 of all or a substantial portion of the exhaust holes 230 can be formed from a single insert while allowing the insert to be easily withdraw. In some configurations, the insert or die can be withdrawn through the distal end 214 of the elbow and the exhaust holes 230 have surfaces that are suitably configured for such a direction of insertion and removal of the insert.

Preferably, the wall thickness (i.e., a distance between the inner surface 234 and the outer surface 240) is approximately 1.5 mm. In such a configuration, the proximal end 232 (i.e., the conical portion in FIG. 14) is approximately 0.5 mm while the distal end 236 (i.e., the trumpet portion in FIG. 14) is approximately 1.0 mm. Other dimensions and configurations are possible. The illustrated configuration has been found to suitably reduce a noise level associated with the air stream exiting the exhaust holes 230.

With reference again to FIG. 2, one or more headgear clips 250 are shown attached to the frame 102. In the illustrated configuration, two headgear clips 250 are secured to the frame 102. The frame 102 generally comprises an ear 252 that is associated with each headgear clip 250. The ears 252 preferably extend generally laterally outward from the inner surface 202 that defines the socket for the elbow 206.

Figure 15:
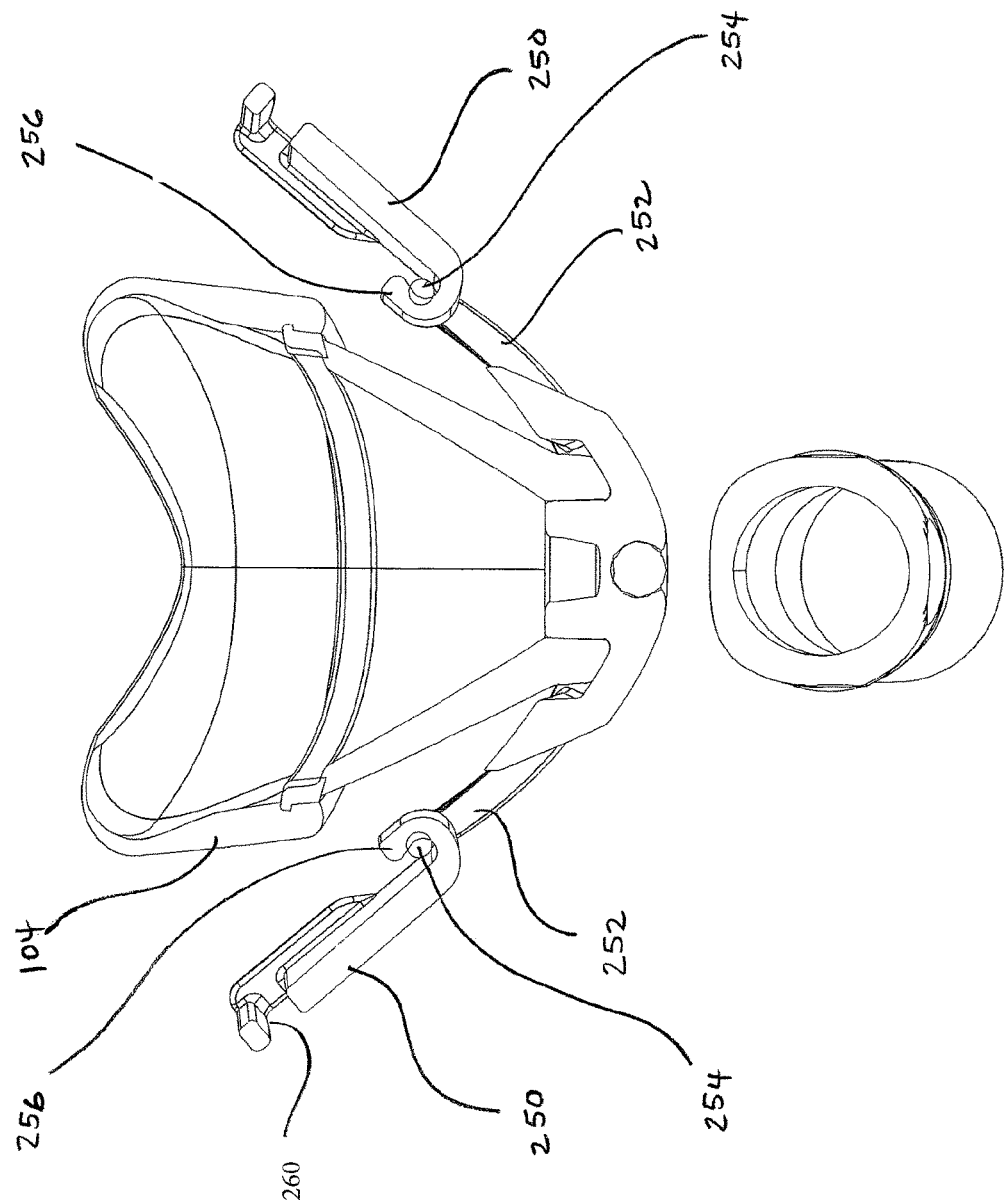
FIG. 15 is sectioned view of the interface assembly taken along the line 15-15 in FIG. 2.

As illustrated in FIG. 15, each of the ears 252 includes a post 254 while each of the clips 250 includes a hook 256. The hook 256 and the post 254 provide an easily connectable and disconnectable configuration. Preferably, the clips 250 are symmetrical such that a single clip can be used on both the left and the right sides of the frame 102.

In some configurations, a slight interference can be provided between the hook 256 and the post 254 such that the hook 256 is less likely to inadvertently disengage during use. In some configurations, the hook 256 and the post 254 can be shaped such that disengagement is easier with the hook 256 in certain angular orientations about the post 254 (e.g., pivoting the hook 256 about the post 254 and away from the seal 106 can allow easier separation due to a profile of the post 254). Moreover, because the hook 256 is capable of pivoting relative to the post 254, the angular orientation of the clip 250 relative to the frame 102 can be varied such that differing shapes of heads can be easily accommodated.

Each clip 250 includes a slot 260 defined trough a main body 262 of the clip 250. The slot 260 is sized and configured to accommodate a lower strap 264 of a headgear assembly 266. Preferably, the lower strap 264 loops through the slot 260 and folds back over itself. More preferably, the lower strap 264 includes a hook and loop fastener portion such that the lower strap 264 loops through the slot 260, folds back over itself and is secured to itself. Other configurations also can be used.

The headgear assembly 266 also comprises a pair of top straps 270 and a pair of upper straps 272. The top straps 270, the upper straps 272 and the bottom straps 264 preferably meet at a central body 274. Moreover, each of the straps 264, 270, 272 preferably terminates with a tab 276 that can form a portion of a hook and loop fastener. The tabs 276 can be ultrasonically welded onto the ends of the straps 264, 270, 272.

Together, the straps 264, 270, 272 and the body 274 define the headgear assembly 266. In some configurations, the headgear assembly comprises a three-layer construction, which includes layers formed of Lycra, foam and UBL (unbroken loop) materials. Advantageously, the UBL material provides a surface onto which the tabs 276 can stick. In some configurations, the thickness of the three-layer construction is about 4 mm.

The top straps 270 can be connected together with a buckle that will sit generally at the top of the head. When combined together with the buckle, the top straps 270 generally define a crown strap. The upper straps 272 loop through slots 280 (see FIG. 2) formed in a t-piece section of the frame 102 and the lower straps 264 loop through the clips 250 as described above. In some configurations, the slots 280 in the t-piece section of the frame 102 have a break in the material defining the slots 280 such that the loop defined by the upper straps 272 can be attached and detached to the frame 102 without separating the tab 276 from the portion of the strap 272 to which the tab 276 is attached with the hook and loop fastener.

In the alternative interface arrangement 100 of FIGS. 17-23, the slots 280 define openings 340 at bottom ends of the slots 280 and have closed ends 342 at the top ends thereof. In particular, a central portion 344 of the frame 102 extends along inner sides of the slots 280 and transitions into an upper portion 346 that defines the closed ends 342 of the slots 280. Outer portions 350 extend along outer sides of the slots 280 and terminate in inwardly-extending tabs 352 that extend toward the central portion 344, but stop short thereof to define the openings 340 of the slots 280. The upper closed ends 342 prevent the upper straps 272 from becoming disconnected from the frame 102 in an upward direction and the tabs 352 inhibit unintentional or undesirable disconnection of the upper straps 272 from the frame 102 in a downward direction.

The body 274 preferably is defined as regions that interconnect the various straps 264, 270, 272 and the regions that taper to the straps 264, 270, 272 to provide reinforcement to the intersections of the straps 264, 270, 272. The body 2374 can be configured to sit below the Inion point of the skull. Such a positioning on the user decreases movement of the headgear assembly 266 when the user turns the head.

Figure 16:
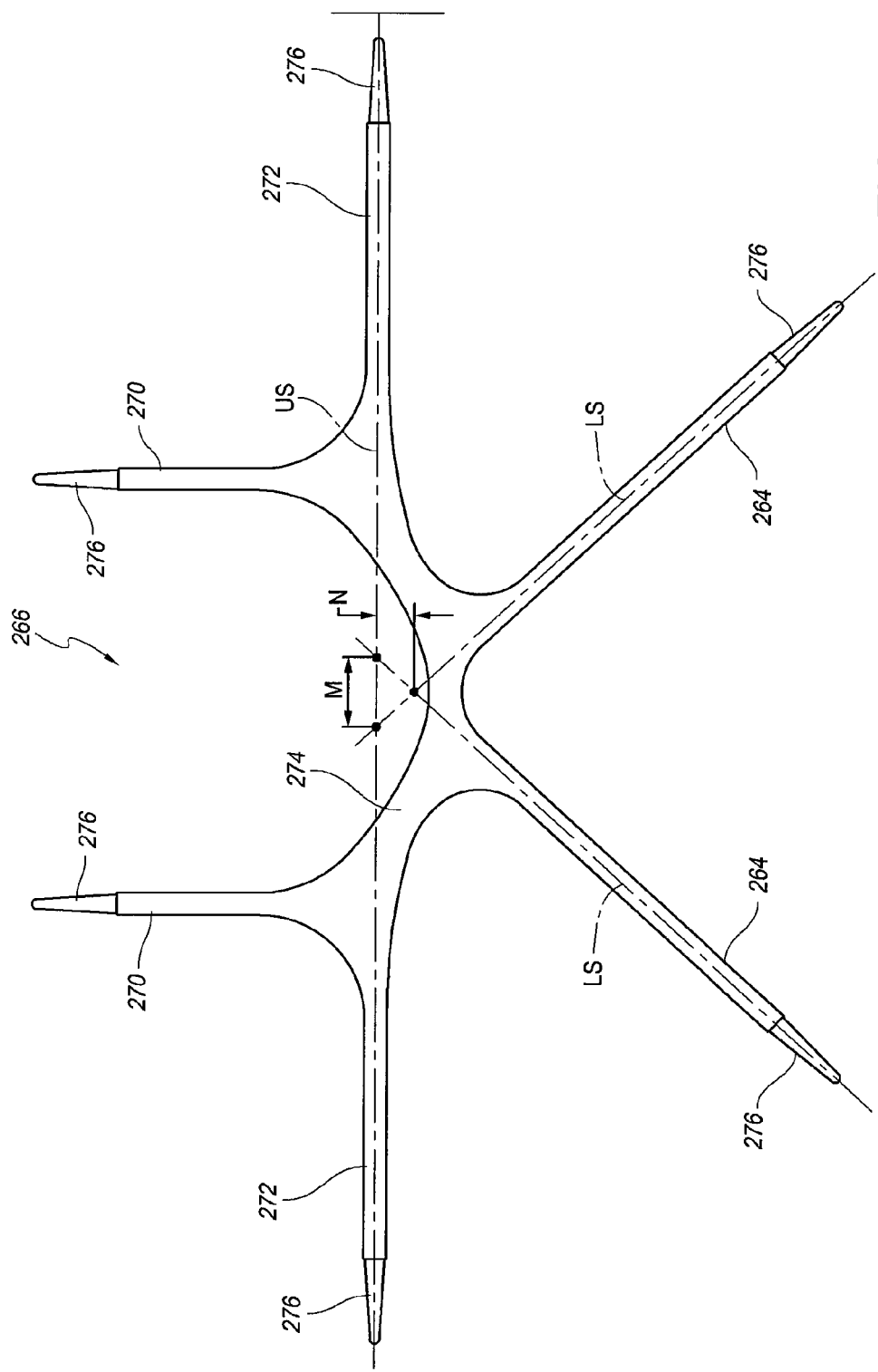
FIG. 16 is an illustration of a headgear assembly used with the interface assembly of FIG. 2 prior to being joined to the frame of the interface assembly of FIG. 2.
Figure 17:
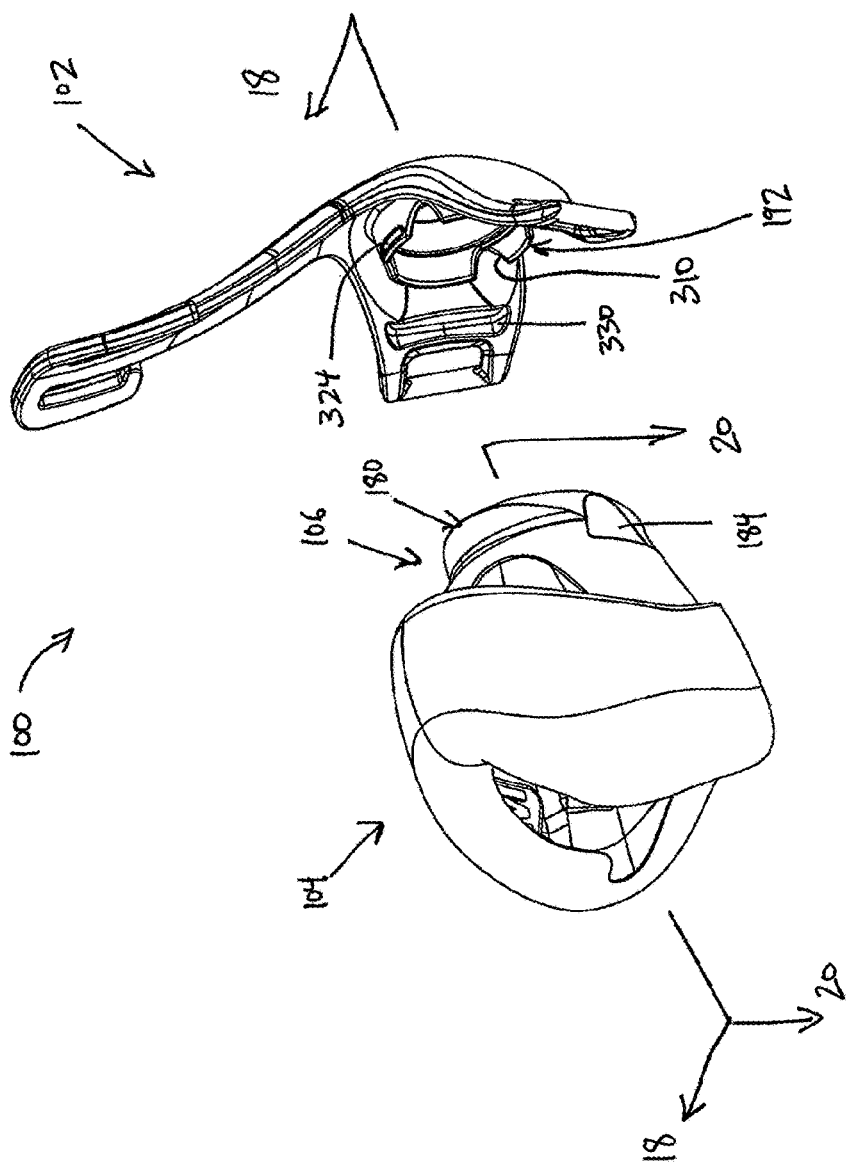
FIG. 17 is a perspective view of an alternative interface assembly with the seal and clip separated from the frame.

Moreover, with the straps attached a three dimensional configuration results from generally straight strap configurations. In other words, as shown in FIG. 16, the lower straps 264 extend in a substantially straight manner from the body 274. As such, a generally central line LS extends along each of the lower straps 264. Similarly, as shown in FIG. 16, the upper straps 272 also extend in a substantially straight manner from the body 274. As such, a generally central line US extends along both the upper straps 272. In the illustrated configuration, the central line US do not intersect the entire body 274. In other words, the body has a portion that is offset from, and not intersected by, the central line US. In some configurations, the generally central lines LS are positioned at an angle relative to the generally central line US. Preferably, the angle is between about 20 degrees and about 50 degrees.

In the illustrated configuration, the lower strap central lines LS intersect at a location between the body 274 and the upper strap central line US. In some configurations, the lower strap central lines LS intersect to the same side of the upper strap central line US as the lower straps 264 are positioned. In some configurations, the intersection of the lower strap central lines LS is offset a distance N from the upper strap central line US. Preferably, the distance M is about 23 mm. In some configurations, the lower strap central lines LS intersect the upper strap central line US at locations that are spaced apart by a distance M. Preferably, the distance M is about 43 mm. Other configurations also are possible.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A seal member for an interface assembly, the seal member configured to fit over a nose of a user in use, the seal member comprising:
   a sidewall extending around a periphery of the seal member and having upper and lower sections, the upper section defining an apex of the seal member shaped to fit over a bridge of the nose of the user in use, the lower section defining left and right corners of the seal member, wherein left and right portions of the lower section of the sidewall proximate to the left and right corners of the seal member, respectively, are thickened relative to adjacent portions of the sidewall that are adjacent to the left and right portions;
   a thickened band positioned along the sidewall and extending from a left side of the apex, over the apex, to a right side of the apex of the sidewall, the thickened band projecting inwardly from an inner surface of the sidewall that faces the user in use;
   a flange extending inwardly from a proximal end of the sidewall, the flange comprising a face contacting surface that is configured to bear against a face of the user and an interior surface opposite the face contacting surface, the flange comprising an edge that at least partially defines an opening, a lip surface disposed at a lower portion of the flange and adapted to contact the face of the user in use at a location above a vermillion border and below nares of the user, a lateral surface disposed at an upper portion of the flange and adapted to extend over a bridge of the nose of the user, and left and right cheek surfaces disposed on the upper portion of the flange and extending between the lip surface and the lateral surface, the left and right cheek surfaces adapted to contact at least two of left and right medial cheek surfaces of the user and left and right lateral nose surfaces of the user; and
   a left thickened panel positioned along a left side of the upper portion of the flange, and a right thickened panel positioned along a right side of the upper portion of the flange, the left and right thickened panels being configured to provide additional pressure pressing the flange against lateral sides of the nose of the user in use;
   wherein each of the left and right thickened panels comprises a substantially trapezoidal pad projecting from the interior surface of the flange away from the face contacting surface, the left and right thickened panels defining locally thickened regions of the flange that are thicker than the remainder of the flange, wherein each of the first and second thickened panels are spaced from the thickened band, and wherein the edge of the opening forms an innermost side of the substantially trapezoidal pad.

2. The seal member according to claim 1, wherein shortest sides of the left and right thickened panels are disposed along the edge of the flange that at least partially defines the opening.

3. The seal member according to claim 1, wherein longest sides of the left and right thickened panels are disposed parallel to the edge of the flange that at least partially defines the opening.

4. The seal member according to claim 1, wherein the left and right thickened panels have top edges angled relative to the edge of the flange, and bottom edges perpendicular to the edge of the flange.

5. A seal member for an interface assembly, the seal member configured to fit over a nose of a user in use, the seal member comprising:
   a sidewall extending around a periphery of the seal member and having upper and lower sections, the upper section defining an apex of the seal member shaped to fit over a bridge of the nose of the user in use;
   a flange extending inwardly from a proximal end of the sidewall, the flange comprising a face contacting surface that is configured to bear against a face of the user and an interior surface opposite the face contacting surface, the flange comprising an edge that at least partially defines an opening, a lip surface disposed at a lower portion of the flange and adapted to contact the face of the user in use at a location below nares of the user, a lateral surface disposed at an upper portion of the flange and adapted to extend over a bridge of the nose of the user, and left and right cheek surfaces disposed on the upper portion of the flange and extending between the lip surface and the lateral surface; and
   a left thickened panel positioned along a left side of the upper portion of the flange, and a right thickened panel positioned along a right side of the upper portion of the flange, the left and right thickened panels being configured to provide additional pressure pressing the flange against lateral sides of the nose of the user in use;
   wherein each of the left and right thickened panels comprises a substantially trapezoidal pad projecting from the interior surface of the flange away from the face contacting surface, the left and right thickened panels defining locally thickened regions of the flange that are thicker than the remainder of the flange, and wherein the edge of the opening forms an innermost side of the substantially trapezoidal pad.

6. The seal member according to claim 5, the lower section of the sidewall defining left and right corners of the seal member, wherein left and right portions of the lower section of the sidewall proximate to the left and right corners of the seal member, respectively, are thickened relative to adjacent portions of the sidewall that are adjacent to the left and right portions.

7. The seal member according to claim 5 additionally comprising a thickened band positioned along the sidewall and extending from a left side of the apex, over the apex, to a right side of the apex of the sidewall, the thickened band projecting inwardly from an inner surface of the sidewall, wherein each of the first and second thickened panels are spaced from the thickened band.

8. The seal member according to claim 5, wherein the left and right cheek surfaces are each adapted to contact at least two of left and right medial cheek surfaces of the user and left and right lateral nose surfaces of the user in use.

9. The seal member according to claim 5, wherein shortest sides of the left and right thickened panels are disposed parallel to the edge of the flange that at least partially defines the opening.

10. The seal member according to claim 5, wherein longest sides of the left and right thickened panels are disposed parallel to the edge of the flange that at least partially defines the opening.

11. The seal member according to claim 5, wherein the left and right thickened panels have top edges angled relative to the edge of the flange, and bottom edges perpendicular to the edge of the flange.

12. A seal member for an interface assembly, the seal member configured to fit over a nose of a user in use, the seal member comprising:
   a sidewall extending around a periphery of the seal member and having upper and lower sections, the upper section defining an apex of the seal member shaped to fit over a bridge of the nose of the user in use;
   a flange extending inwardly from a proximal end of the sidewall, the flange comprising a face contacting surface that is configured to bear against a face of the user an interior surface opposite the face contacting surface, and an edge that at least partially defines an opening; and
   a left thickened panel positioned on the interior surface along a left side of an upper portion of the flange, and a right thickened panel positioned on the interior surface along a right side of the upper portion of the flange, the left and right thickened panels configured to provide additional pressure pressing the flange against lateral sides of the nose of the user in use, and wherein the edge of the opening forms an innermost side of each of the left and right thickened panels.

13. The seal member according to claim 12, the flange comprising a lip surface disposed at a lower portion of flange and adapted to contact the face of the user in use at a location below nares of the user, a lateral surface disposed at an upper portion of the flange and adapted to extend over a bridge of the nose of the user, and left and right cheek surfaces disposed on the upper portion of the flange and extending between the lip surface and the lateral surface.

14. The seal member according to claim 12, wherein each of the left and right thickened panels comprises a substantially trapezoidal pad projecting from the interior surface of the flange away from the face contacting surface, the left and right thickened panels defining locally thickened regions of the flange that are thicker than the remainder of the flange.

15. The seal member according to claim 12, wherein the lower section of the sidewall defines left and right corners of the seal member, wherein left and right portions of the lower section of the sidewall proximate to the left and right corners of the seal member, respectively, are thickened relative to adjacent portions of the sidewall that are adjacent to the left and right portions.

16. The seal member according to claim 12 additionally comprising a thickened band positioned along the sidewall and extending from a left side of the apex, over the apex, to a right side of the apex of the sidewall, the thickened band projecting inwardly from an inner surface of the sidewall, wherein each of the first and second thickened panels are spaced from the thickened band.

17. The seal member according to claim 13, wherein the left and right cheek surfaces are adapted to contact at least two of left and right medial cheek surfaces of the user and left and right lateral nose surfaces of the user in use.

18. The seal member according to claim 13, wherein shortest sides of the left and right thickened panels are disposed along the edge of the flange that at least partially defines the opening.

19. The seal member according to claim 13, wherein shortest sides of the left and right thickened panels are disposed parallel to the edge of the flange that at least partially defines the opening.

20. The seal member according to claim 13, wherein longest sides of the left and right thickened panels are disposed parallel to edge of the flange that at least partially defines the opening.

* * * * *

UNITED STATES PATENT AND TRADEMARK OFFICE
CERTIFICATE OF CORRECTION

PATENT NO. : 10,413,693 B2
APPLICATION NO. : 15/610484
DATED : September 17, 2019
INVENTOR(S) : Craig Robert Prentice Page 1 of 1

It is certified that error appears in the above-identified patent and that said Letters Patent is hereby corrected as shown below:

In the Specification

Column 7, Lines 35-36, delete "PCT/M2012/000858" and insert --PCT/IB2012/000858--.

In the Claims

Column 17, Line 44, Claim 12, delete "user" and insert --user,--.

Signed and Sealed this
Twenty-eighth Day of July, 2020

Andrei Iancu
*Director of the United States Patent and Trademark Office*